US010695474B2

(12) United States Patent
Granegger et al.

(10) Patent No.: US 10,695,474 B2
(45) Date of Patent: Jun. 30, 2020

(54) METHOD AND APPARATUS FOR DETERMINING AORTIC VALVE OPENING

(71) Applicants: St Vincent's Hospital Sydney Limited, Darlinghurst, New South Wales (AU); Medical University of Vienna, Vienna (AT)

(72) Inventors: Marcus Granegger, Perchtoldsdorf (AT); Francesco Moscato, Vienna (AT); Heinrich Schima, Vienna (AT); Christopher Simon Hayward, Longueville (AU)

(73) Assignees: St Vincent's Hospital Sydney Limited, Darlinghurst, New South Wales (AU); Medical University of Vienna, Vienna (AT)

( * ) Notice: Subject to any disclaimer, the term of this patent is extended or adjusted under 35 U.S.C. 154(b) by 429 days.

(21) Appl. No.: 15/513,519

(22) PCT Filed: Sep. 22, 2015

(86) PCT No.: PCT/AU2015/050566
§ 371 (c)(1),
(2) Date: Mar. 22, 2017

(87) PCT Pub. No.: WO2016/044889
PCT Pub. Date: Mar. 31, 2016

(65) Prior Publication Data
US 2018/0228955 A1 Aug. 16, 2018

(30) Foreign Application Priority Data
Sep. 23, 2014 (AU) ................ 2014903794

(51) Int. Cl.
*A61M 1/12* (2006.01)
*A61M 1/10* (2006.01)

(52) U.S. Cl.
CPC .......... *A61M 1/1086* (2013.01); *A61M 1/122* (2014.02); *A61M 1/101* (2013.01);
(Continued)

(58) Field of Classification Search
USPC .......................................... 600/17
See application file for complete search history.

(56) References Cited

U.S. PATENT DOCUMENTS

| 6,066,086 A | 5/2000 | Antaki et al. |
| 6,949,066 B2 | 9/2005 | BearnsOn et al. |

(Continued)

FOREIGN PATENT DOCUMENTS

| JP | 2009-297174 A | 7/2011 |
| JP | 2016-533772 A | 11/2016 |
| WO | 2003057280 A1 | 7/2003 |
| WO | 2013184932 A1 | 12/2013 |
| WO | 2014015300 A1 | 1/2014 |
| WO | 2014044287 A1 | 3/2014 |

OTHER PUBLICATIONS

Kim Pennings et al. "Estimation of a left ventricular pressure in patients with a continuous flow LVAD" Academic Medical Centre, Amsterdam; Eindhoven University of Technology; LifeTec Group BV, Eindhoven; Poster session presented at Mate Poster Award 2014 : 19th Annual Poster Contest; Published: Jan. 1, 2014—2 pages.

(Continued)

*Primary Examiner* — Nicole F Lavert
(74) *Attorney, Agent, or Firm* — Fish IP Law, LLP

(57) ABSTRACT

Apparatus for determining opening of an aortic valve of a biological subject, the apparatus including an electronic processing device that determines a pump speed of a ventricular assist device that is assisting cardiac function of the biological subject, analyses the pump speed to determine a pump speed indicator at least partially indicative of changes in pump speed and uses the pump speed indicator to determine an opening indicator indicative of opening of the aortic valve.

16 Claims, 18 Drawing Sheets

(52) U.S. Cl.
CPC ....... *A61M 1/1005* (2014.02); *A61M 2205/33* (2013.01); *A61M 2205/3303* (2013.01); *A61M 2205/3334* (2013.01); *A61M 2205/3365* (2013.01)

(56) References Cited

U.S. PATENT DOCUMENTS

| | | | |
|---|---|---|---|
| 8,506,470 | B2 | 8/2013 | LaRose et al. |
| 2010/0087742 | A1 | 4/2010 | Bishop et al. |
| 2010/0305692 | A1* | 12/2010 | Thomas ............... A61M 1/10 623/3.1 |
| 2014/0114202 | A1 | 4/2014 | Hein et al. |
| 2014/0152944 | A1 | 6/2014 | Zhao |
| 2015/0151032 | A1 | 6/2015 | Voskoboynikov et al. |
| 2018/0228955 | A1 | 8/2018 | Granegger et al. |

OTHER PUBLICATIONS

Published Japanese Translation of PCT International Application No. 2005-514973 pp. 1-12.

Published Japanese Translation of PCT International Application No. 2004-501678 p. 1-75.

ISA/AU, International Search Report, Int'l Appln No. PCT/AU2016/050566, dated Nov. 2, 2015 (3 pages).

Granegger, M., et al., "Assessment of Aortic Valve Opening During Rotary Blood Pump Support Using Pump Signals," Artficial Organs. Apr. 2014, 38(4), pp. 290-297.

Corey J. Bishop, Nathan O. Mason; Abdallah G. Kfoury; Robert Lux; Sandi Stoker; Kenneth Horton, Stephen E. Clayson; Brad Rasmusson; Bruce B. Reid; A novel non-invasive method to assess aortic valve opening in HeartMate II left ventricular assist device patients using a modified Karhunen-Loève transformation; The Ournal of Heart and Lung Transplantation; Jan. 2010; pp. 27-31; vol. 29, No. 1; Murray, Utah, US.

Marcus Granegger; Heinrich Schima; Daniel Zimpfer; Francesco Moscato; Assessment of Aortic Valve Opening During Rotary Blood Pump Support Using Pump Signals; Artificial Organs; 2014; pp. 290-297; vol. 38 (4); Artificial Organs; Center for Medical Physics and Biomedical Engineering, Medical University of Vienna; †Department of Cardiac Surgery, Medical University of Vienna; and ‡Ludwig-Boltzmann—Cluster for Cardiovascular Research, Vienna, Austria.

* cited by examiner

METHOD AND APPARATUS FOR DETERMINING AORTIC VALVE OPENING

BACKGROUND OF THE INVENTION

The present invention relates to a method and apparatus for determining opening of an aortic valve of a biological subject, and to a method and apparatus for controlling operation of a ventricular assist device based on aortic valve opening.

DESCRIPTION OF THE PRIOR ART

The reference in this specification to any prior publication (or information derived from it), or to any matter which is known, is not, and should not be taken as an acknowledgment or admission or any form of suggestion that the prior publication (or information derived from it) or known matter forms part of the common general knowledge in the field of endeavour to which this specification relates.

Patients with impaired left ventricular function typically have low cardiac output and consequent poor exercise capacity. Some patients with particularly severe dysfunction require mechanical left ventricular assistance to "bridge" them to heart transplantation. Continuous flow pumps using a rotating impeller are both durable and reliable in providing cardiac output for patients with restoration of functional capacity and exercise capability to allow meaningful rehabilitation before transplantation.

Rotary pumps use an impeller rotating at a fixed speed (depending on pump design between a rotary speed of 2000 rpm and 10000 rpm respectively) and rely on variations in preload and afterload to affect pump output. Flow is related to head pressure, which equates to the difference between aortic and left ventricular pressure, with an increase in preload or decrease in afterload leading to an increase in output.

At present, no cfLVAD in clinical use has a physiological pump flow controller incorporated into the device. Research is underway to develop a controller that can automatically adjust pump flow in response to changes in the patient's hemodynamic state. In order to do this, inputs regarding pump and hemodynamic parameters are required. However, such information is difficult to obtain without implanting a sensor into the subject, which is impractical as a long term solution. In particular, implanted sensors create difficulties with thrombosis, malfunction, calibration and cost.

It has been demonstrated that pump flow parameters can be used to derive hemodynamic parameters. However, the derivation of the parameters depends on the opening state of the aortic valve, and so it is useful to be able to determine aortic valve state when a cfLVAD is in use for the purpose of blood pressure calculations, as well as to allow for measurement of contractility and relaxation using load independent algorithms. Additionally, some opening of the aortic valve is generally beneficial as this can lead to reduced instances of thromboembolic events, valve leaflet fusion, leaflet degradation and aortic valve insufficiency, and potentially also gastrointenstinal bleeding events.

"Assessment of Aortic Valve Opening During Rotary Blood Pump Support Using Pump Signals" by Marcus Granegger et al *Artif Organs* 2014; 38(4):290-297, "A novel non-invasive method to assess aortic valve opening in HeartMate II left ventricular assist device patients using a modified Karhunen-Loeve transformation" by Bishop et al, *J Heart Lung Transplant* 2010; 29(1):27-31 and "Robust aortic valve non-opening detection for different cardiac conditions" by Ooi et al, *Artif Organs* 2014; 38(3):E57-E67. describe algorithms to determine opening of the aortic valve based on the shape of the systolic portion of the pump flow signal. However, a major limitation of these techniques is the binary classification into an open or closed aortic valve, and this in turn is of only limited assistance when calculating hemodynamic parameters.

SUMMARY OF THE PRESENT INVENTION

In one broad form the present invention seeks to provide apparatus for determining opening of an aortic valve of a biological subject, the apparatus including an electronic processing device that:
  a) determines a pump speed of a ventricular assist device that is assisting cardiac function of the biological subject;
  b) analyses the pump speed to determine a pump speed indicator at least partially indicative of changes in pump speed; and,
  c) uses the pump speed indicator to determine an opening indicator indicative of opening of the aortic valve.

Typically the opening indicator is indicative of at least one of a degree, duration and timing of opening of the aortic valve.

Typically the pump speed indicator is at least one of:
  a) indicative of rates of change of pump speed; and,
  b) a distribution based on rates of change of pump speed.

Typically the distribution is at least one of:
  a) a frequency distribution; and,
  b) a power spectral density distribution.

Typically the electronic processing device:
  a) compares the pump speed indicator to at least one threshold; and,
  b) determines the opening indicator in response to the results of the comparison.

Typically the pump speed indicator is a distribution, and wherein the electronic processing device determines the threshold based on a maximum value of the distribution.

Typically the pump speed indicator is a power spectral density distribution and wherein the electronic processing device:
  a) determines a maximum power frequency corresponding to the frequency having a maximum power in the power spectral density distribution; and,
  b) determines the threshold based on the maximum power frequency.

Typically the pump speed indicator is a distribution of rates of change of pump speed and wherein the electronic processing device:
  a) determines a portion of the distribution greater than the threshold; and,
  b) determines the opening indicator using the portion.

Typically the electronic processing device:
  a) calculates an area under curve for the portion; and,
  b) uses the area under curve to determine the opening indicator.

Typically the electronic processing device:
  a) determines a pump speed of the ventricular assist device for a plurality of cardiac cycles; and,
  b) determines an opening indicator for at least one of the plurality of cardiac cycles.

Typically the electronic processing device:
  a) determines the flow rate of blood through the ventricular assist device; and,
  b) uses the rate of flow of blood to identify individual cardiac cycles.

Typically the electronic processing device identifies individual cardiac cycles from flow rate minima.

Typically the electronic processing device at least one of:
a) records the opening indicator; and,
b) displays a representation of the opening indicator.

Typically the electronic processing device uses the opening indicator to at least partially determine a hemodynamic parameter value indicative of at least one of:
a) an intra-cardiac pressure;
b) an atrial pressure;
c) a ventricular filling pressure;
d) a pulmonary capillary wedge pressure;
e) a ventricular end diastole pressure;
f) a mean arterial pressure;
g) ventricular contractility properties; and,
h) ventricular relaxation properties.

Typically the ventricular assist device includes a rotating impeller, and wherein the pump speed corresponds to a rate of rotation of the impeller.

Typically the electronic processing device determines the pump speed at least one of:
a) in accordance with signals received from a sensor; and,
b) by receiving pump speed data from a ventricular assist device controller.

Typically the electronic processing device:
a) determines pump speed data indicative of the speed of the ventricular assist device pump; and,
b) performs a frequency transform on the speed data to determine the speed indicator.

Typically the electronic processing device:
a) filters the pump speed data to remove high frequency components; and,
b) determines the pump speed indicator using the filtered pump speed data.

Typically the electronic processing device:
a) applies a window function to the pump speed data to create a window of pump speed data; and,
b) generates a power spectral density distribution using the window of pump speed data.

Typically the electronic processing device controls the ventricular assist device in accordance with the opening indicator.

Typically the electronic processing device intermittently controls the pump speed in accordance with the opening indicator.

Typically the electronic processing device at least one of:
a) selectively reduces the pump speed to cause opening of the aortic valve; and,
b) selectively increases the pump speed to reduce opening of the aortic valve.

Typically the electronic processing device:
a) determines opening indicators over multiple cardiac cycles;
b) compares a number of cardiac cycles since the aortic valve last opened to a threshold; and,
c) selectively controls the pump speed in response to results of the comparison.

Typically the electronic processing device progressively reduces the pump speed over successive cardiac cycles until at least one of:
a) the aortic valve opens; and,
b) a minimum pump speed is reached.

In another broad form the present invention seeks to provide a method for determining opening of an aortic valve of a biological subject, the method including, in an electronic processing device:
a) determining a pump speed of a ventricular assist device that is assisting cardiac function of the biological subject;
b) analysing the pump speed to determine a pump speed indicator at least partially indicative of changes in pump speed; and,
c) using the pump speed indicator to determine an opening indicator indicative of opening of the aortic valve.

In another broad form the present invention seeks to provide apparatus for controlling a ventricular assist device, the apparatus including an electronic processing device that:
a) determines a pump speed of the ventricular assist device over at least one cardiac cycle;
b) analyses the pump speed to determine a pump speed indicator at least partially indicative of changes in pump speed;
c) uses the pump speed indicator to determine whether the aortic valve has opened; and,
d) controls the ventricular assist device depending on whether the aortic valve has opened.

In another broad form the present invention seeks to provide a method of controlling a ventricular assist device, the method including:
a) determining a pump speed of the ventricular assist device over at least one cardiac cycle;
b) analysing the pump speed to determine a pump speed indicator at least partially indicative of changes in pump speed;
c) using the pump speed indicator to determine whether the aortic valve has opened; and,
d) controlling the ventricular assist device depending on whether the aortic valve has opened.

In another broad form the present invention seeks to provide apparatus for use with a ventricular assist device that is assisting cardiac function of a biological subject, the apparatus including an electronic processing device that:
a) determines a pump speed of the ventricular assist device over at least one cardiac cycle;
b) analyses the pump speed to determine a pump speed indicator at least partially indicative of changes in pump speed; and,
c) uses the pump speed indicator to at least one of:
   i) determine an opening indicator indicative of opening of the aortic valve; and,
   ii) control the ventricular assist device.

In another broad form the present invention seeks to provide a method for use with a ventricular assist device that is assisting cardiac function of a biological subject, the method including:
a) determining a pump speed of the ventricular assist device over at least one cardiac cycle;
b) analysing the pump speed to determine a pump speed indicator at least partially indicative of changes in pump speed; and,
c) using the pump speed indicator to at least one of:
   i) determine an opening indicator indicative of opening of the aortic valve; and,
   ii) control the ventricular assist device.

BRIEF DESCRIPTION OF THE DRAWINGS

An example of the present invention will now be described with reference to the accompanying drawings, in which:—

DETAILED DESCRIPTION OF THE PREFERRED EMBODIMENTS

Figure 1:
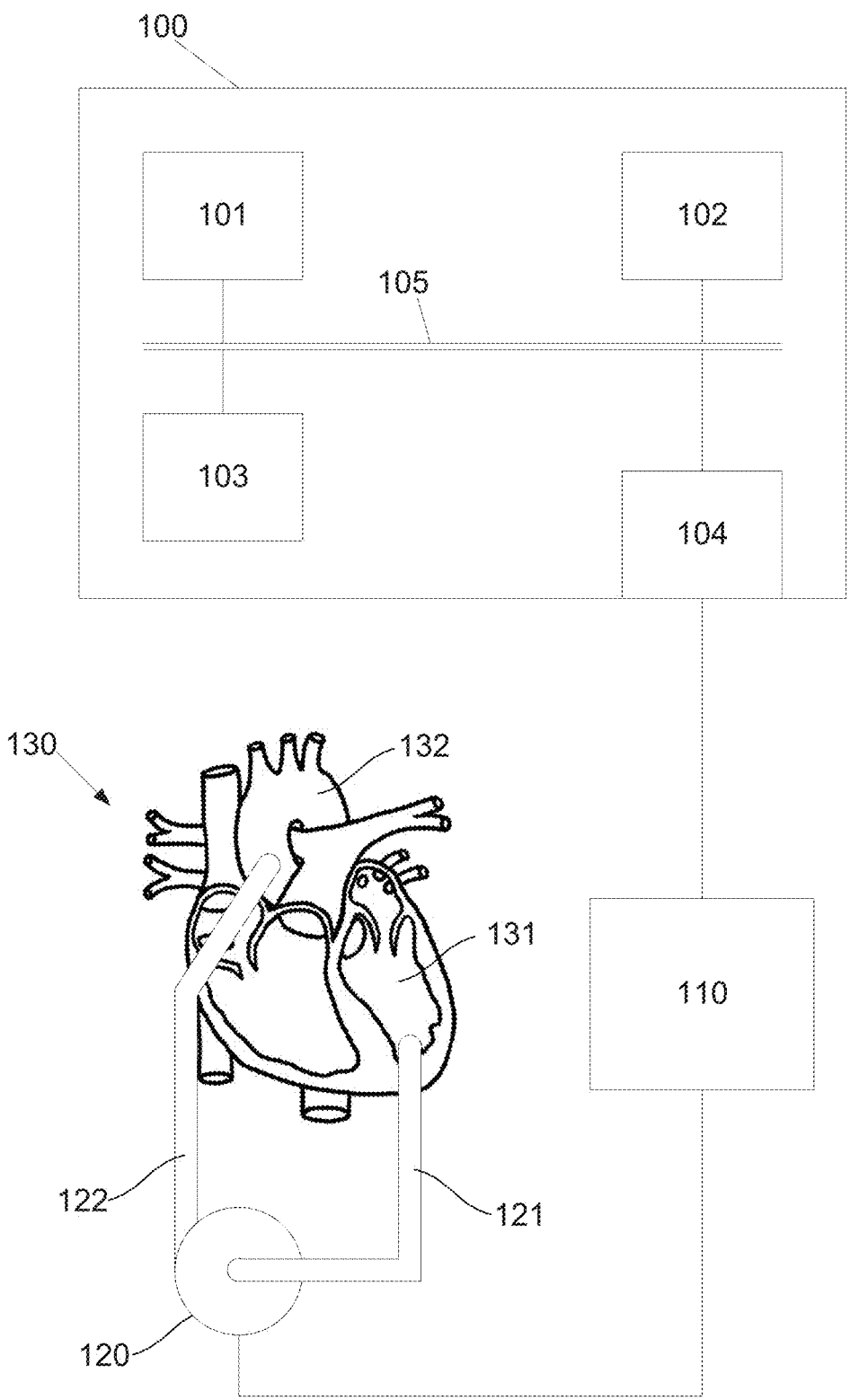
FIG. 1 is a schematic diagram of an example of apparatus for use with a ventricular assist device (VAD)

An example of an apparatus for use with a VAD will now be described with reference to FIG. 1.

In this example, the apparatus includes a processing system 100 that is coupled to a VAD 120, which is in turn connected to the heart 130 of a subject. In this example, the VAD is coupled via respective inlet and outlet cannulas 121, 122 to the left ventricle 131 and aorta 132, and is therefore functioning as a left ventricular assist device (LVAD), although this is not essential and similar techniques to those described can also be applied to right ventricular assist devices (RVADs) coupled to the right ventricle and pulmonary artery. The VAD is a continuous flow VAD (cfVAD) in which an impeller is continuously rotated within a cavity, to thereby pump blood from the ventricle into the aorta. The VAD 120 can be a standard VAD known in the art, such as a Heartware HVAD, Ventracor Ventrassist, or the like, and this will not therefore be described in further detail.

In this example, the processing system 100 is coupled to the VAD 120 via a controller 110, via a wired or wireless connection. The controller 110 operates to control the VAD and in particular control rotation of the impeller and optionally monitor operating characteristics of the VAD. This arrangement is not essential and alternatively the processing system 100 and controller 110 can be implemented as a single piece of hardware, although it will be appreciated that use of a separate processing system that interfaces with an existing controller can reduce regulatory requirements needed for implementation. It will also be appreciated that the controller 110 could include both controlling and monitoring functionality and hardware, with the processing system 100 being periodically connected to the controller as required.

Figure 2:
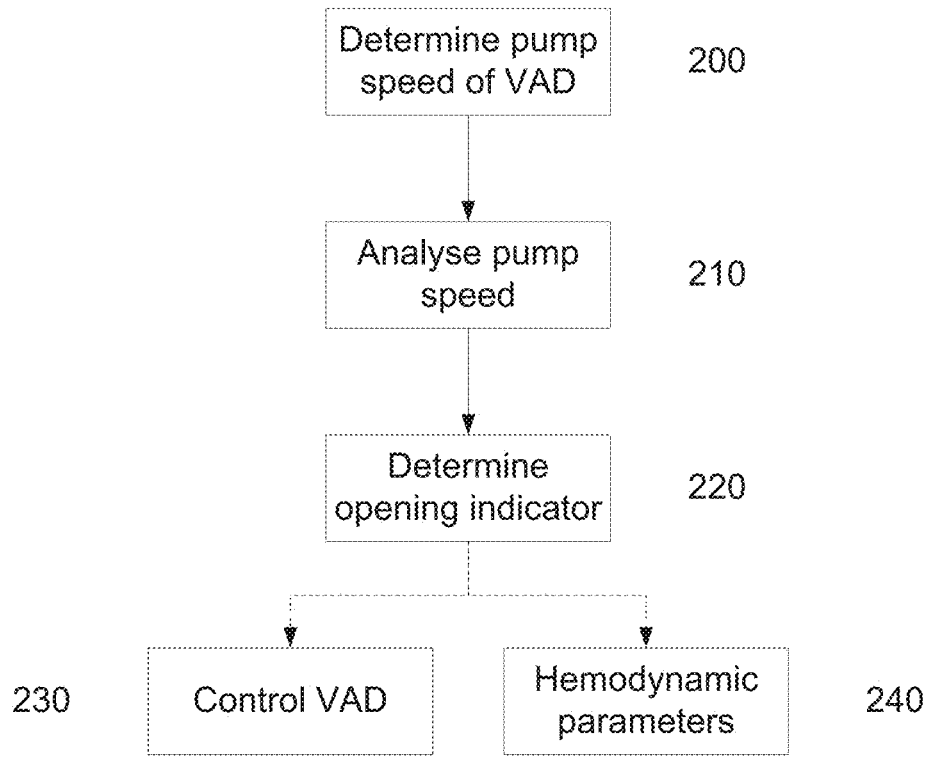
FIG. 2 is a flow chart of an example of a method for determining aortic valve opening.

In use, the processing system 100 includes an electronic processing device, such as a microprocessor, that is adapted to determine an opening indicator indicative of opening of the aortic valve and then optionally use this to control operation of the VAD, or determine hemodynamic parameter values, such as blood pressure parameter values, as will now be described with reference to FIG. 2.

In this example, at step 200, the electronic processing device determines a pump speed of the VAD 120. The pump speed, and in particular the rate of rotation of the impeller, can be determined in any suitable manner and can be obtained from sensors incorporated within the VAD 120, or alternatively could be derived from operating characteristics of the VAD 120. The pump speed could be calculated by the electronic processing device or alternatively could be received as pump speed data from the controller 110, depending on the preferred implementation.

At step 210, the electronic processing device analyses the pump speed to determine a a pump speed indicator at least partially indicative of changes in pump speed. This can be achieved in any suitable manner, but typically involves identifying cardiac cycles corresponding to individual heart beats, and then analysing these to determine rates of change of pump speed during the cardiac cycles. The pump speed indicator can be of any appropriate form, and could include a pump speed waveform, waveform gradient information, or the like. In one particular example, the pump speed waveform is in the form of a frequency distribution, such as a power spectral density distribution, indicative of a distribution of the frequencies of the changes in pump speed, as will be described in more detail below.

Figure 3A:
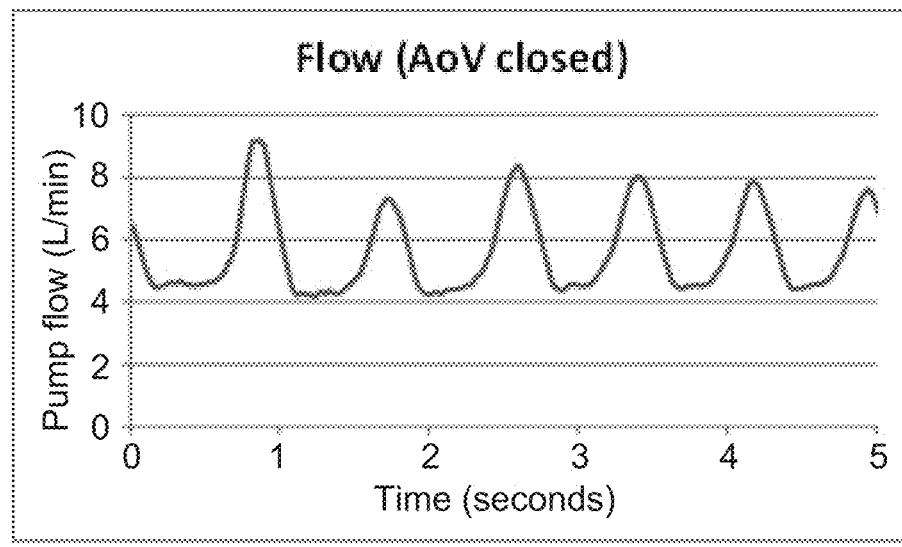
FIG. 3A is a graph of an example of raw flow data from a ventricular assist device with the aortic valve closed.
Figure 3B:
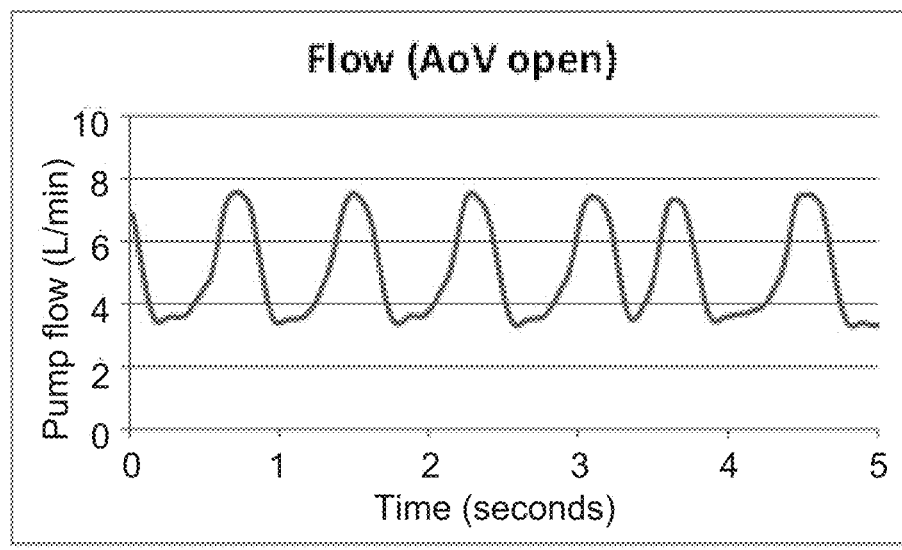
FIG. 3B is a graph of an example of raw flow data from a ventricular assist device with the aortic valve open.

At step 220, the electronic processing device uses the pump speed indicator to determine an opening indicator indicative of opening of the aortic valve. In this regard, opening of the aortic valve allows blood to flow from the left ventricle into the aorta, thereby bypassing the VAD 120. This in turn causes a change in the pressure head across the VAD 120, thereby altering the pump flow. An example of this is shown in FIGS. 3A and 3B, which shows pump flows for a subject with the aortic valve closed and open, respectively. In particular, in FIG. 3A it can be seen that the LVAD flow waveform is more peaked in the closed aortic valve state, whereas with the valve opening during ventricular contraction, the waveform is broader as shown in FIG. 3B. However, pump flow in currently clinical used LVAD systems is estimated based on the speed and current signal. To identify and quantify the described characteristics of the flow signal certain requirements such as frequency content for such a pump flow signal are required.

Figure 3C:
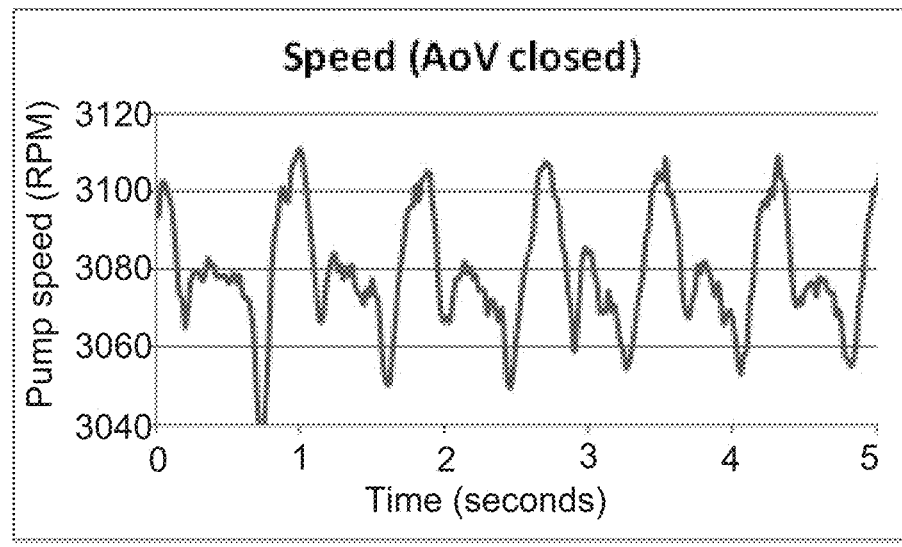
FIG. 3C is a graph of an example of pump speed data from a ventricular assist device with the aortic valve closed.
Figure 3D:
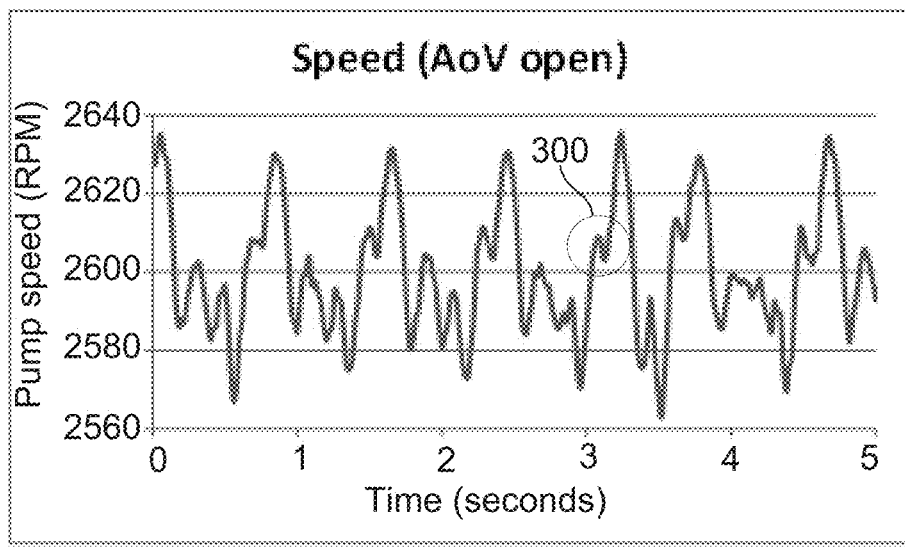
FIG. 3D is a graph of an example of pump speed data from a ventricular assist device with the aortic valve open.

However, the pump pressure head and consequently the pump flow also influences pump speed. In particular, as the pressure across the pump decreases, there is a corresponding drop in the rate of impeller rotation. This is shown in the pump speed waveforms shown in FIGS. 3C and 3D, which in particular demonstrate a marked "notch" 300 mid-way through the contraction phase of the waveform. Whilst a similar notch may be present when the aortic valve remains closed, this tends to be less marked and more typically situations at the end of the contraction phase. Thus, a change in the pump speed, such as a change in the rate of rotation of an impeller, can be used to identify when the aortic valve opens.

Additionally, it has been determined that opening of the aortic valve leads to a more rapid change in pump speed than other typical events in the cardiac cycle, such as contraction of the ventricle. Accordingly, in addition to simply examining the pump speed, the electronic processing device more usefully examines the rate of change of pump speed, to identify events having a significantly higher rate of change in speed than other events within the cardiac cycle. This can be achieved in any appropriate manner, such as examining gradients of the pump speed waveform, but can advantageously be achieved using a frequency analysis, as will be described in more detail below.

In any event, by analysing the pump speed indicator, this allows the electronic processing device to generate an opening indicator, indicative of opening of the aortic valve. This opening indicator could simply be an indication of whether the aortic valve is open or closed but more typically at least partially quantifies the opening, for example by being at least partially indicative of a degree, duration and/or timing of opening of the aortic valve. Thus, the opening indicator could specify a degree of opening, such as whether the aortic valve is closed, open or partially open, and could indicate a duration of each degree of opening. The opening indicator could be in the form of one or more alphanumeric codes, or could be provided in the form of a graphical representation, for example as a graph mapped to the cardiac cycle, allowing a medical practitioner to more easily identify how the aortic valve is opening over one or more cardiac cycles.

Once determined, the opening indicator could be recorded for later use or displayed to an operator, for example to allow for a medical assessment of the subject. Additionally and/or alternatively the opening indicator can be used in controlling the VAD and/or determining hemodynamic parameters at steps 230 and 240, respectively, as will be described in more detail below.

Accordingly, the above described process allows for opening of the aortic valve to be detected using the pump speed, and in particular changes in the pump speed of a VAD. As pump speed of a VAD is a parameter that is typically already measured in commercial devices, this in turn allows for opening of the aortic valve to be determined without requiring the use of additional sensors. This therefore provides a straightforward mechanism for determining aortic valve opening. Assessment of aortic valve opening can be used to provide clinically useful information regarding the subject and can therefore be useful from a therapeutic perspective, for example to assess a subject's cardiac function, and determine whether intervention may be desirable. Additionally, this could be used in conjunction with operation of the VAD, for example to allow operation of the VAD to be controlled, and to assist in deriving additional parameters, such as hemodynamic information, including blood pressure parameters or the like.

A number of further features will now be described.

In the above described example, the processing system 100 includes at least one microprocessor 101, a memory 102, an optional input/output device 103, such as a keyboard and/or display, and an external interface 104, interconnected via a bus 105 as shown. In this example the external interface 104 can be utilised for connecting the processing system 100 to the controller 110 and optionally to peripheral devices, such as the communications networks, databases, or the like. Although a single external interface 104 is shown, this is for the purpose of example only and in practice, multiple interfaces using various methods (eg. Ethernet, serial, USB, wireless or the like) may be provided.

In use, the microprocessor 101 executes instructions in the form of applications software stored in the memory 102 to allow pump speed data to be received from the controller 110 and used to calculate an opening indicator, and optionally to generate control signals that can be transferred to the controller 110, allowing operation of the VAD 120 to be controlled. The applications software may include one or more software modules, and may be executed in a suitable execution environment, such as an operating system environment, or the like.

Accordingly, it will be appreciated that the processing system 100 may be formed from any suitable processing system, such as a suitably programmed computer system, PC, web server, network server, or the like. However, it will also be understood that the processing system could be any electronic processing device such as a microprocessor, microchip processor, logic gate configuration, firmware optionally associated with implementing logic such as an FPGA (Field Programmable Gate Array), or any other electronic device, system or arrangement.

Additionally and/or alternatively, the processing system 100 and controller 110 can be integrated into a single device. Thus, for example, the method of FIGS. 2A and 2B could be performed using an existing heart pump controller modified to allow for the opening indicator to be calculated. This could be achieved using a firmware and/or software upgrade or the like, as will be appreciated by persons skilled in the art.

Figure 4A:
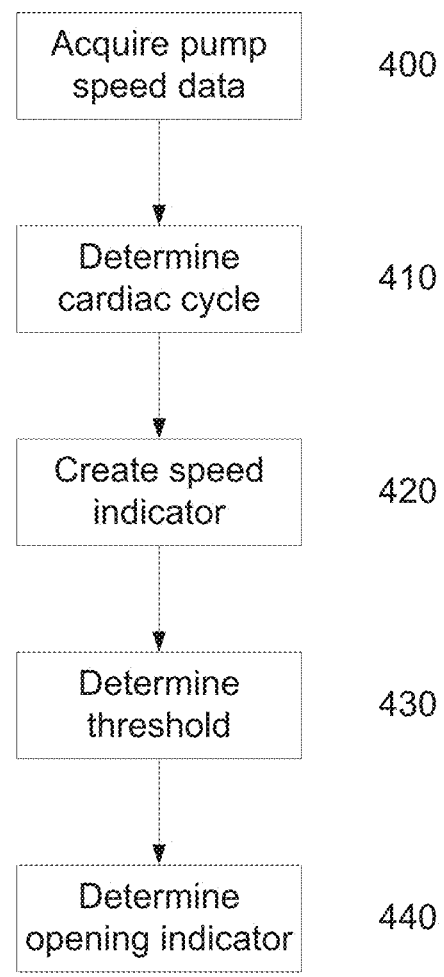
FIG. 4A is a flow chart of a second example of a method for determining aortic valve opening.
Figure 4B:
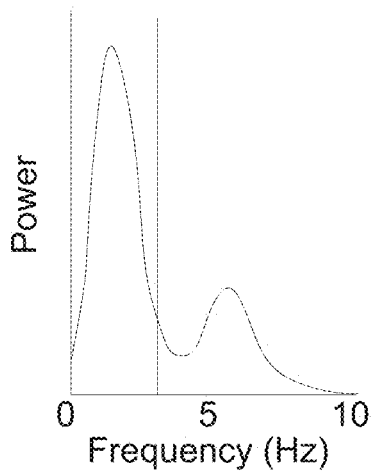
FIG. 4B is a graph of an example of the frequency response of a VAD during aortic valve opening.

A further example of a method for determining an opening indicator will now be described with reference to FIG. 4.

In this example, at step 400, the electronic processing device determines the pump speed by acquiring pump speed data. The pump speed data can be obtained either in accordance with signals received from a sensor or by receiving pump speed data from a ventricular assist device controller 110, depending on the preferred implementation.

The pump speed data is used to determine the pump speed for a plurality of cardiac cycles, with the electronic processing device determining an opening indicator for at least one of the plurality of cardiac cycles. To achieve this, at step 410, the electronic processing device determines a cardiac cycle either by examining the maximum or minimum pump speeds or alternatively using the flow rate of blood through the ventricular assist device, as will be described in more detail below.

At step 420, the electronic processing device determines the pump speed indicator. In this regard, the pump speed indicator can be of any appropriate form and is typically indicative of rates of change of pump speed or a distribution based on rates of change of pump speed. In one specific example, the distribution is a frequency distribution such as a power spectral density distribution, in which case the electronic processing device performs a frequency transform on the pump speed data, such as a Fast Fourier Transform (FFT), to thereby determine the pump speed indicator.

At step 430, the electronic processing device compares the pump speed indicator to at least one threshold. The threshold can represent a particular rate of change of pump speed or frequency in the frequency distribution, above which the change is likely to have been caused by aortic valve opening as opposed to some other factor. Thus, this allows the processing device to examine the pump speed indicator and use this to set the threshold, making the threshold specific to the subject and even the current cardiac cycle. This helps reduce the likelihood of inaccurate assessment, whilst ensuring that the methodology works for a range of different subjects in a range of different conditions. It will be appreciated however that the threshold could be determined in other manners, such as by studying valve opening in a reference population.

At step 440, the electronic process device uses the result of the comparison to determine the opening indicator. In one example, when the pump speed indicator is a distribution based on rates of change of pump speed the electronic processing device determines a portion of the distribution greater than the threshold and determines the opening indicator using this portion, for example by using this to assess and hence quantify the degree and/or duration of opening of the aortic valve, as will be described in more detail below.

The electronic processing device then typically records and/or displays the opening indicator. Additionally, and/or alternatively, the electronic processing device uses the opening indicator to at least partially determine a hemodynamic parameter value, such as an intra-cardiac pressure, an atrial pressure, a ventricular filling pressure, a pulmonary capillary wedge pressure, a ventricular end diastole pressure, and, a mean arterial pressure. This can be achieved in conjunction with other information, such as pressure parameters derived from examination of pump flow.

Figure 5:
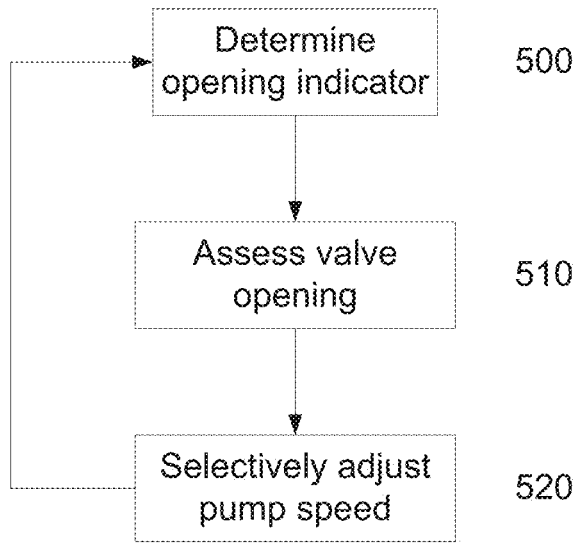
FIG. 5 is a flow chart of an example of a method for controlling a VAD based on aortic valve opening.

The electronic processing device can also control the ventricular assist device in accordance with the opening indicator. In one example this is achieved by at least partially reducing the pump speed to cause opening of the aortic valve. An example of this process will now be described with reference to FIG. 5.

In this example, at step 500 the opening indicator is determined, for example using the process described above with respect to steps 200 to 220. At step 510, the electronic processing device assesses the valve opening and then selectively adjusts the pump speed at step 520. For example, if it is determined that the valve has not opened for some time, the electronic processing device may cause the VAD pump speed to be reduced, which in turn helps increase the likelihood of the aortic valve opening by increasing the ventricular pressure. Alternatively, the electronic processing device may cause the VAD pump speed to be increased, for example to reduce opening of the valve, or once sufficient opening has occurred. Such control of pump speed may not be performed continuously and could be performed intermittently or periodically. For example, it might be that this particular pump speed control protocol is only used for a limited period of time each day, depending on the requirements of the subject. It will also be appreciated that controlling of pump speed will also typically take into account other requirements, such as exercise levels or the like, and that these may override potential changes in pump speed performed solely for the purpose of facilitating aortic valve opening.

This procedure is typically performed over multiple cardiac cycles, with the electronic processing device comparing a number of cardiac cycles since the aortic valve last opened to a threshold and selectively controls the pump speed in response to results of the comparison. As part of this process, the electronic processing device typically progressively reduces the pump speed over successive cardiac cycles until the aortic valve opens or a minimum pump speed is reached, or alternatively progressively increases the pump to reduce valve opening or until a maximum pump speed is reached. Controlling the VAD in this manner can be used to ensure that at least some aortic valve opening occurs, which may help reduce incidences of gastrointestinal bleeding, or the like. Similarly and conversely, the algorithm may be used to increase the pump speed (decreasing the likelihood of aortic valve opening) to provide increased pump support, to a maximum speed or to the occurrence of any episodes of suction, or the like.

Figure 6:
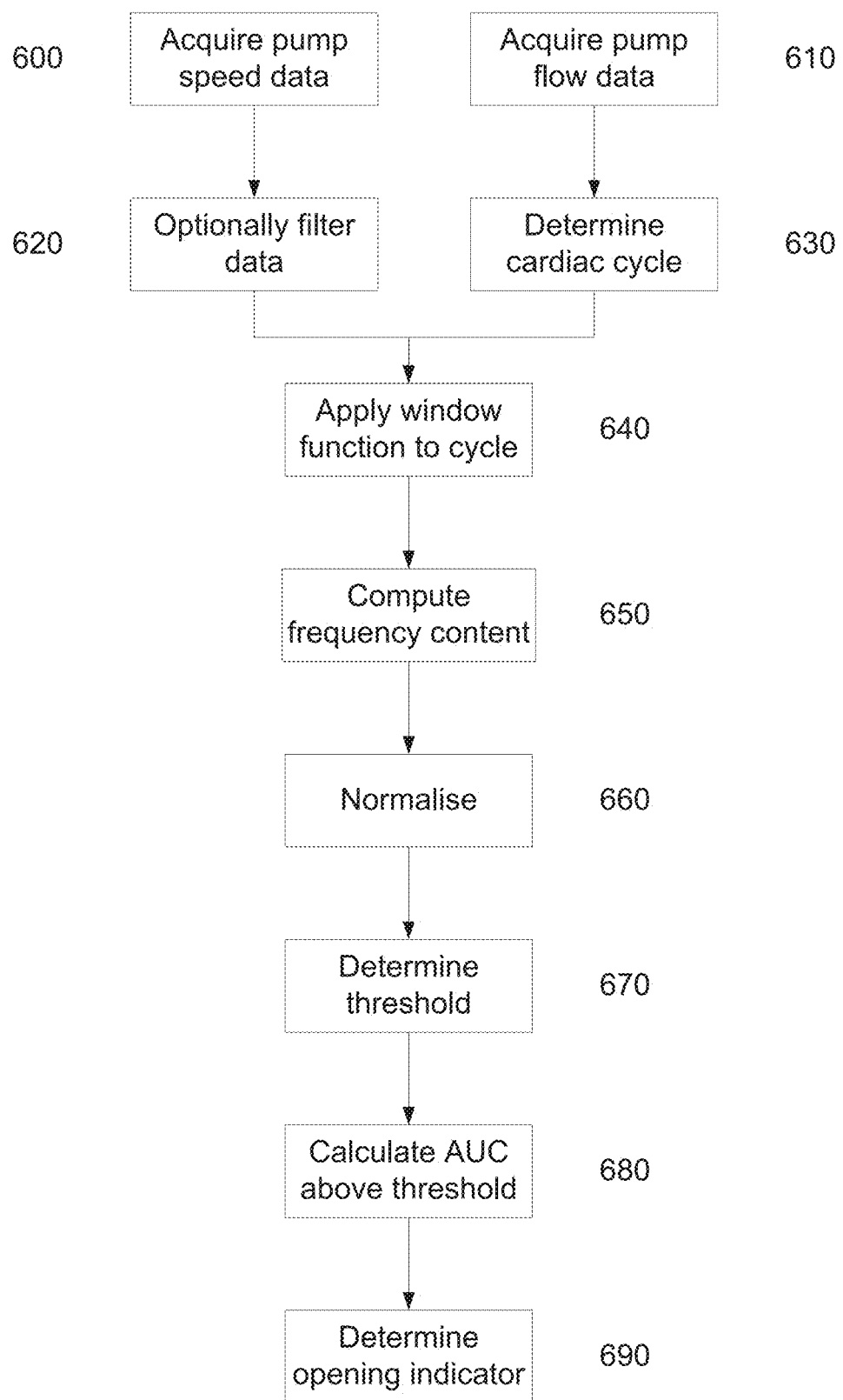
FIG. 6 is a flow chart of a specific example of a method for determining aortic valve opening.

A further more in depth example of the process of determining an opening indicator will now be described with reference to FIG. 6.

In this example, the process is performed over multiple cardiac cycles, with the electronic processing device receiving synchronized pump speed data and pump flow data from the VAD controller 110 at steps 600 and 610 respectively.

Before analysing the pump speed data, the electronic processing device typically pre-processes the pump speed data to make sure it is suitable for analysis. This processing can include filtering the pump speed data at step 620 to remove high frequency components. In one example, the speed data is low pass filtered with a cut off frequency of 12 Hz to reduce the effect of noise and potential aliasing effects.

At step 630 the flow data is analysed to identify individual cardiac cycles, for example using flow rate maxima or minima, with these being used to identify individual cardiac cycles within the pump speed data.

At step 640, a window function, such as a Hanning window, is applied to the pump speed data for each cardiac cycle, to create a window of pump speed data in which beginning and end portions of the cardiac cycle are reduced in magnitude to focus the analysis on parts of the cardiac cycle where the aortic valve opening is expected to be found.

At step 650, the frequency content is computed by applying an FFT, power spectral density (PSD) or other suitable frequency transformation to the data. At step 660, the PSDs for each cardiac cycle are normalised, by determining the mean value of all PSDs at a certain speed setting and then normalising with the highest power corresponding to 1 dB/Hz. This is performed to reduce effects of beats with different number of samples, for example due to different heart rates, and is useful for the purpose of comparison between different heart beats, but is not essential.

At step 670 a threshold is determined. In this instance, with the pump speed indicator in the form of a distribution the electronic processing device determines the threshold based on a maximum value in the distribution. In particular, the electronic processing device determines a maximum power frequency corresponding to the frequency having a maximum power in the power spectral distribution and determines the threshold based on the maximum power frequency. This can be performed for each individual beat, or alternatively can be performed based on a mean PSD calculated over a number of beats and is typically limited to frequencies below 3.5 Hz. The threshold is then determined to be twice the maximum value.

At step 680, the electronic processing device determines a portion of the PSD above the threshold and then calculates an area under curve (AUC) for the portion. The AUC correlates with the degree of opening and can therefore be used to determine the opening indicator at step 690, which is then stored for use as required.

Figure 7:
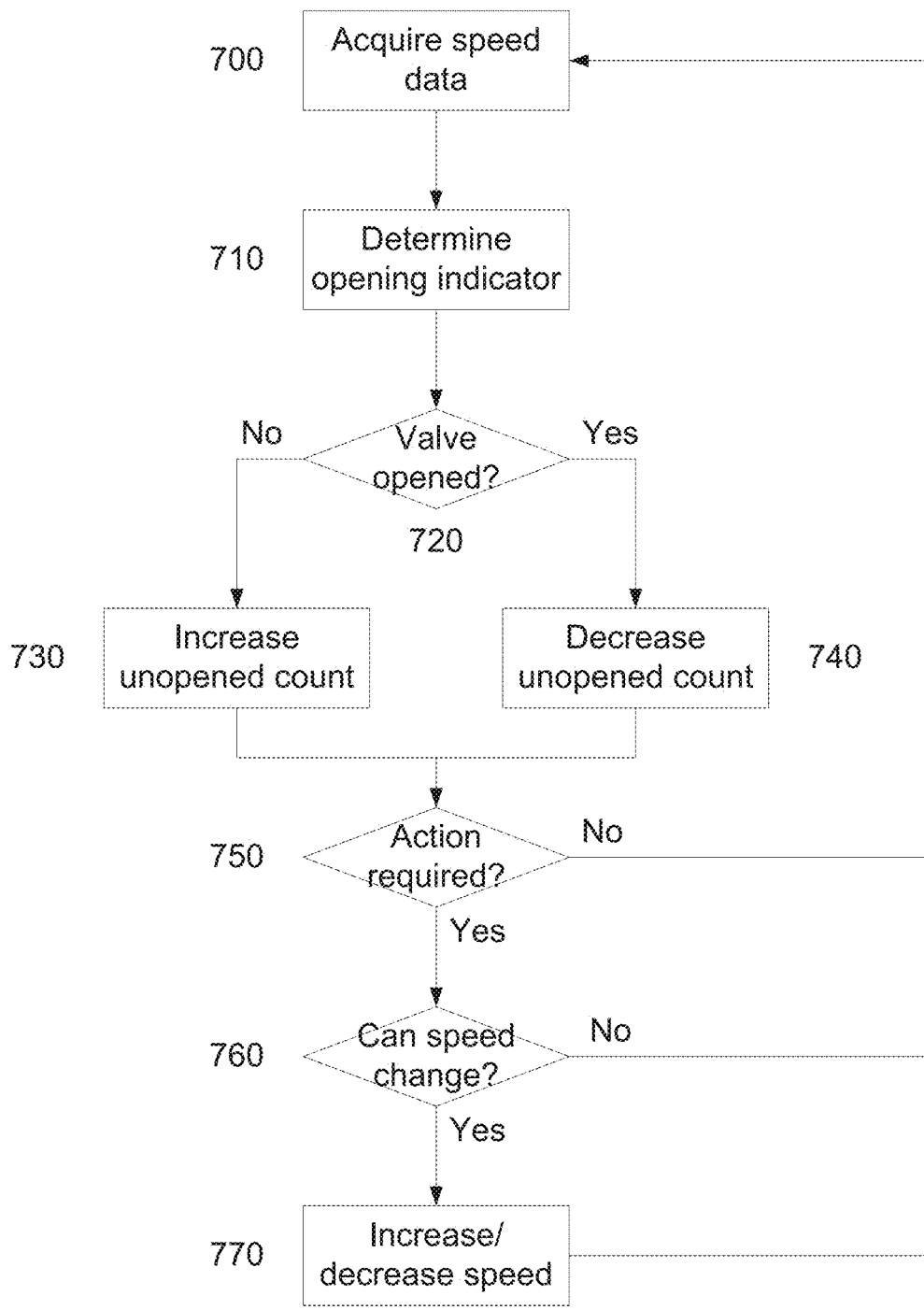
FIG. 7 is a flow chart of a specific example of a method for controlling a VAD based on aortic valve opening.

An example of the process for controlling the VAD will now be described in more detail with reference to FIG. 7.

In this example, at step 700, the speed data is acquired and used to generate the opening indicator at step 710, using the above described method. At step 720, the electronic processing device determines if the valve is open, and if not, an unopened count is increased at step 730, otherwise the count is decreased at step 740.

At step 750 the unopened count is used to determine if action is required. This could be performed in any appropriate manner, and could involve comparing the unopened count to one or more thresholds. For example, this could include comparing the unopened count to an opening threshold which represents a set number of cardiac cycles over which it is desired to have at least one aortic valve opening event. In this case, if the unopened count is greater than the opening threshold, this indicates it is desired to take action to assist in opening the aortic valve. Alternatively, if the opening indicator falls below a closing threshold, this could indicate that the valve is opening too much, meaning the pump is operating ineffectively or insufficiently, meaning action may be taken to avoid or reduce opening of the valve.

If it is determined no action is required, the process returns to step 700, allowing a new opening indicator to be determined.

Otherwise it is determined if the pump speed can change at step 760, for example to determine if the pump speed is within acceptable limits that can accommodate further adjustment. For example, if the current pump speed corresponds to a minimum speed, then a further reduction in pump speed would be prevented, whilst if the current pump speed corresponds to a maximum pump speed, this can be used to prevent an increase in pump speed.

If it is determined that the pump speed can change, then this is adjusted at step 770, either by increasing the speed to reduce the likelihood of valve opening, or to reduce the speed to increase the likelihood of valve opening. Following this, or if there is no change, the process returns to step 700 allowing further speed data to be collected.

Accordingly, the above described process monitors aortic valve opening and in the event that the valve does not open over a set number of cardiac cycles, the pump speed can be progressively reduced either until a valve opening event occurs, or a minimum set speed is reached. Conversely, this also allows the pump speed to be progressively increased to reduce valve opening, until a maximum pump speed is reached. As previously mentioned, this control process could be applied intermittently, and/or in conjunction with other control techniques, depending on the preferred implementation.

EXPERIMENTAL STUDY

Figure 8A:
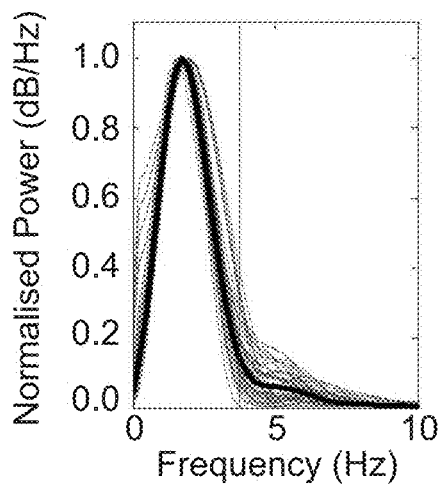
FIGS. 8A to 8V are graphs of example power spectral densities measured for a number of subjects.
Figure 8B:
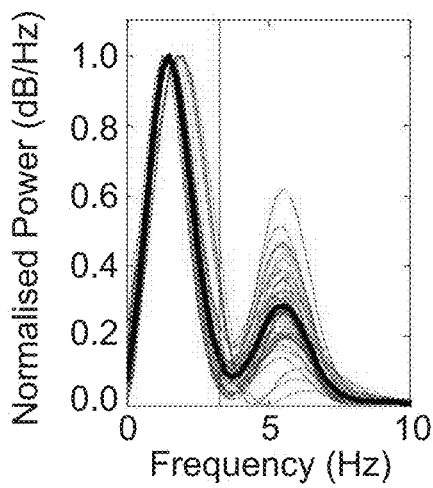
Figure 8C:
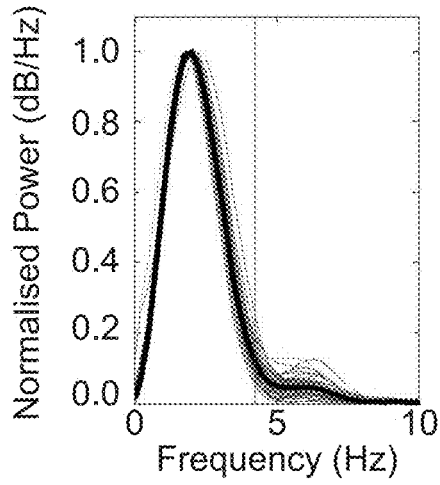
Figure 8D:
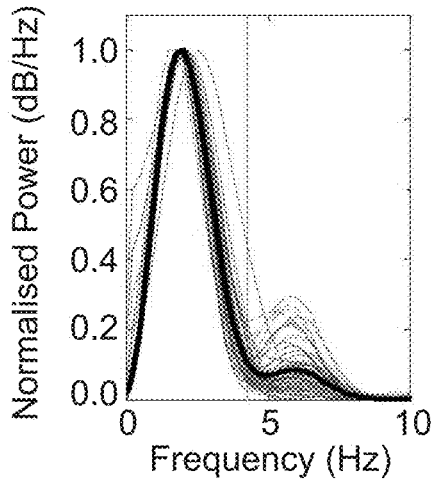
Figure 8E:
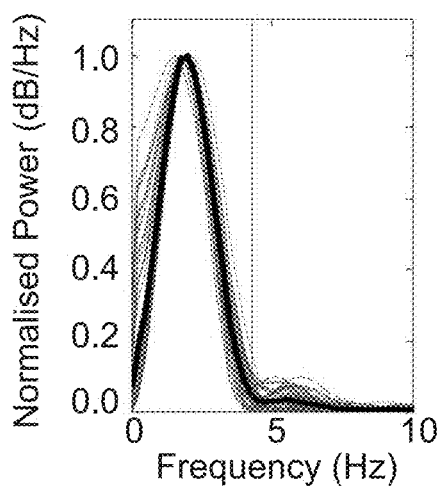
Figure 8F:
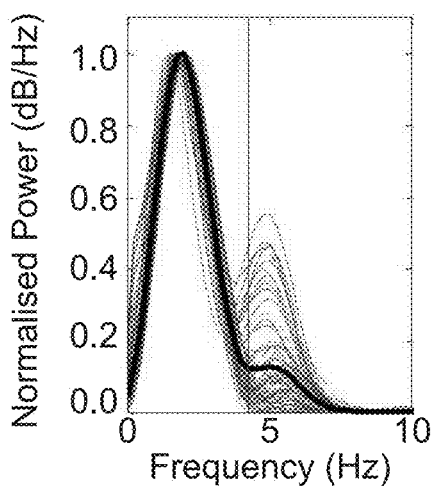
Figure 8G:
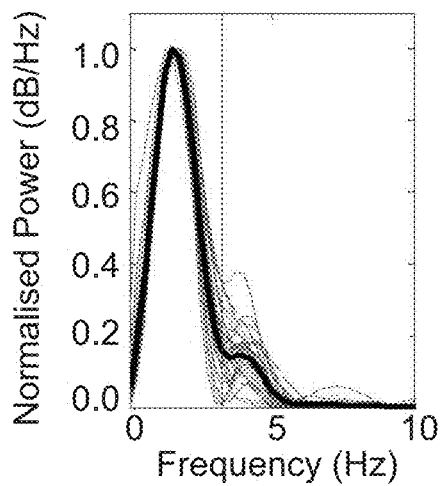
Figure 8H:
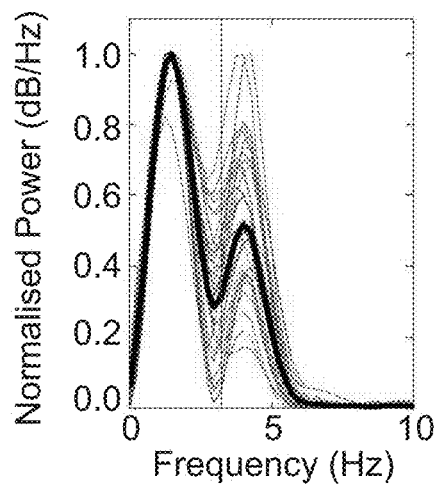
Figure 8I:
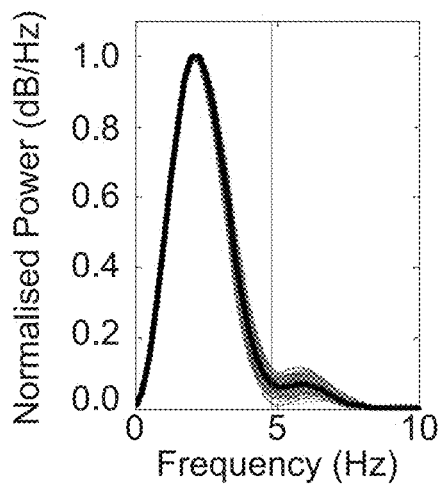
Figure 8J:
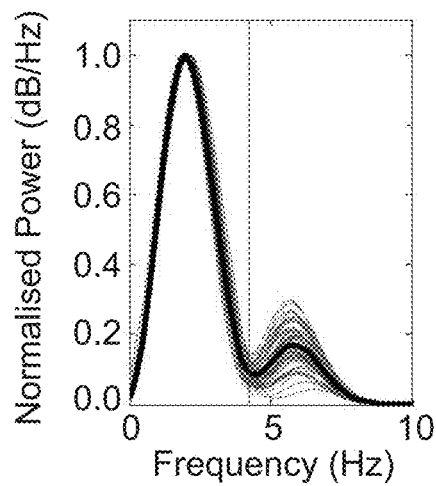
Figure 8K:
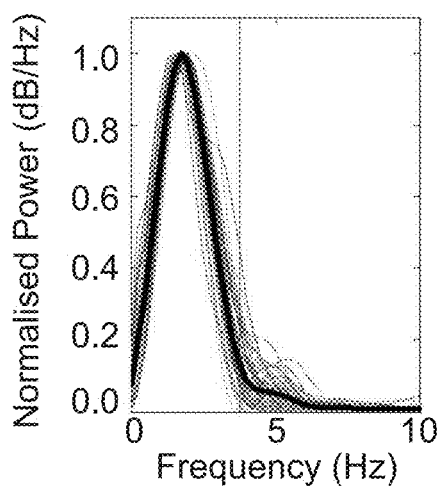
Figure 8L:
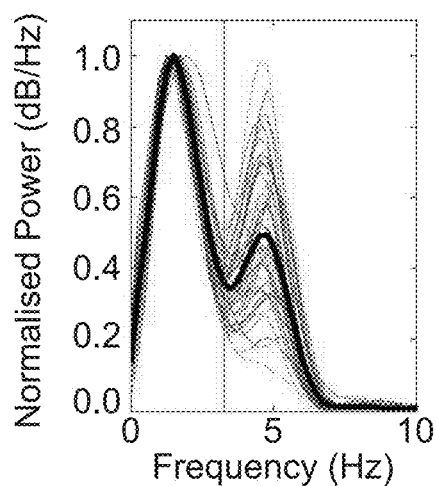
Figure 8M:
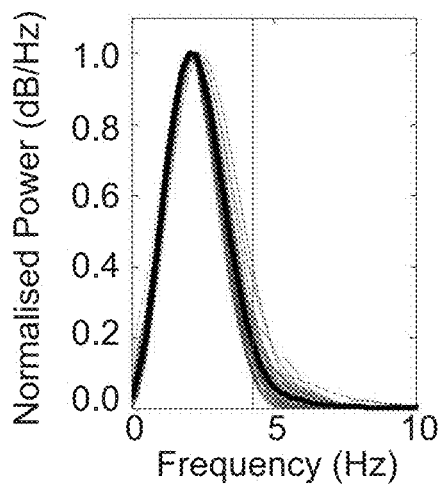
Figure 8N:
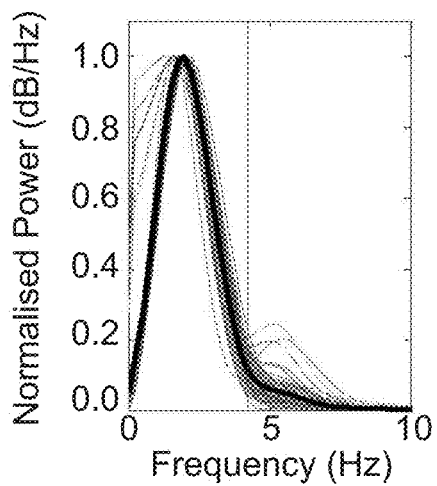
Figure 8O:
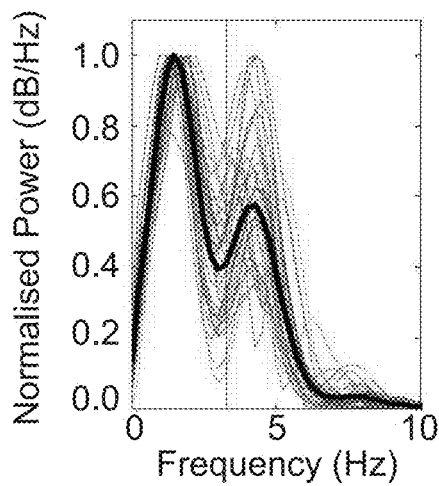
Figure 8P:
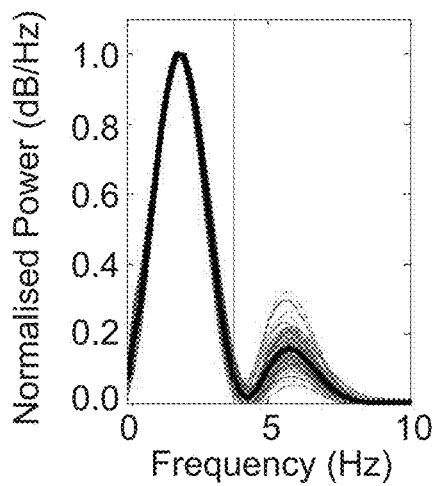
Figure 8Q:
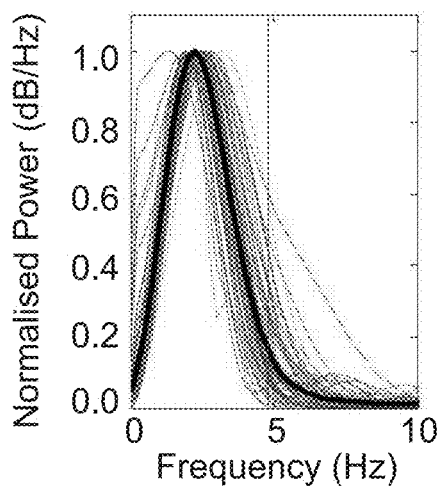
Figure 8R:
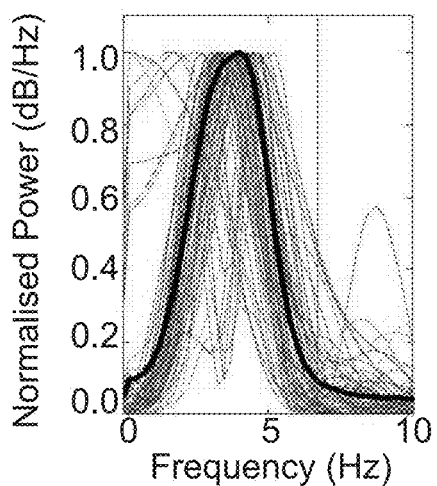
Figure 8S:
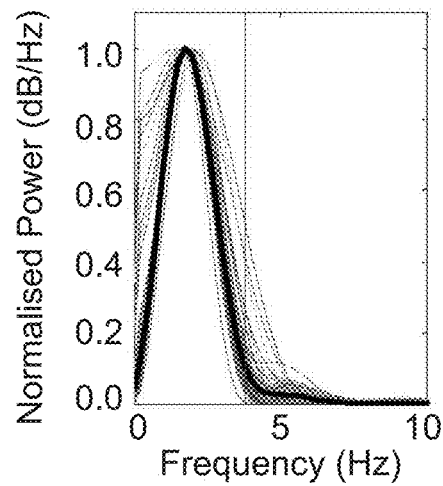
Figure 8T:
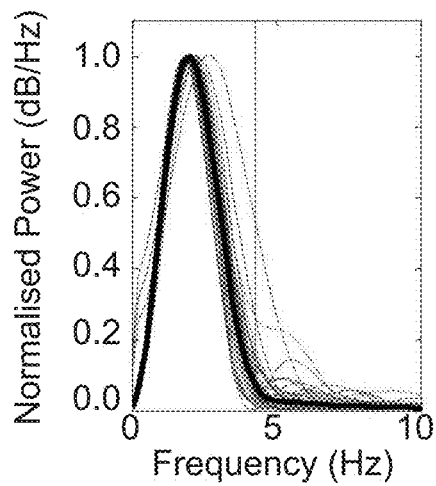
Figure 8U:
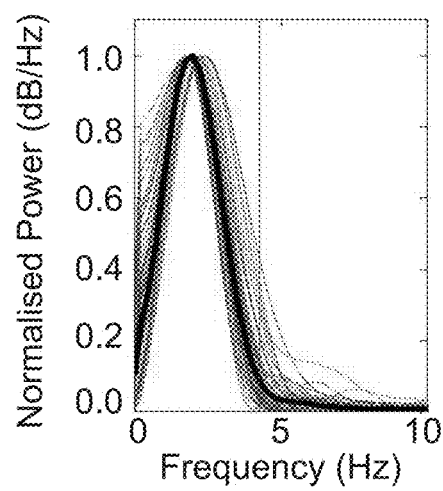
Figure 8V:
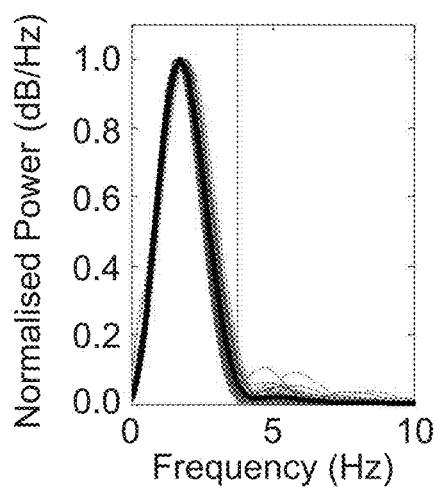

In order to demonstrate the effectiveness of the pump speed in assessing opening events, a study was performed in which data was collected from fifteen patients, with power spectral densities being derived and classified according to whether the aortic valve was open or closed as determined using echocardiography. The results are shown in FIGS. 8A to 8V, as summarised in Table 1 below.

TABLE 1

| FIG. | Patient | Valve State |
|---|---|---|
| 8A | 1 | Closed |
| 8B | 1 | Open |
| 8C | 2 | Closed |
| 8D | 2 | Open |
| 8E | 3 | Closed |
| 8F | 3 | Open |
| 8G | 4 | Closed |
| 8H | 4 | Open |
| 8I | 5 | Closed |
| 8J | 5 | Open |
| 8K | 6 | Closed |
| 8L | 6 | Open |
| 8M | 7 | Closed |
| 8N | 7 | Open |
| 8O | 8 | Open |
| 8P | 9 | Open |
| 8Q | 10 | Closed |
| 8R | 12 | Closed |
| 8S | 12 | Closed |
| 8T | 13 | Closed |
| 8U | 14 | Closed |
| 8V | 15 | Closed |

The results clearly demonstrate a significantly higher contribution to higher frequencies in the PSD when the aortic valve is open compared to when the valve is closed.

Figure 9:
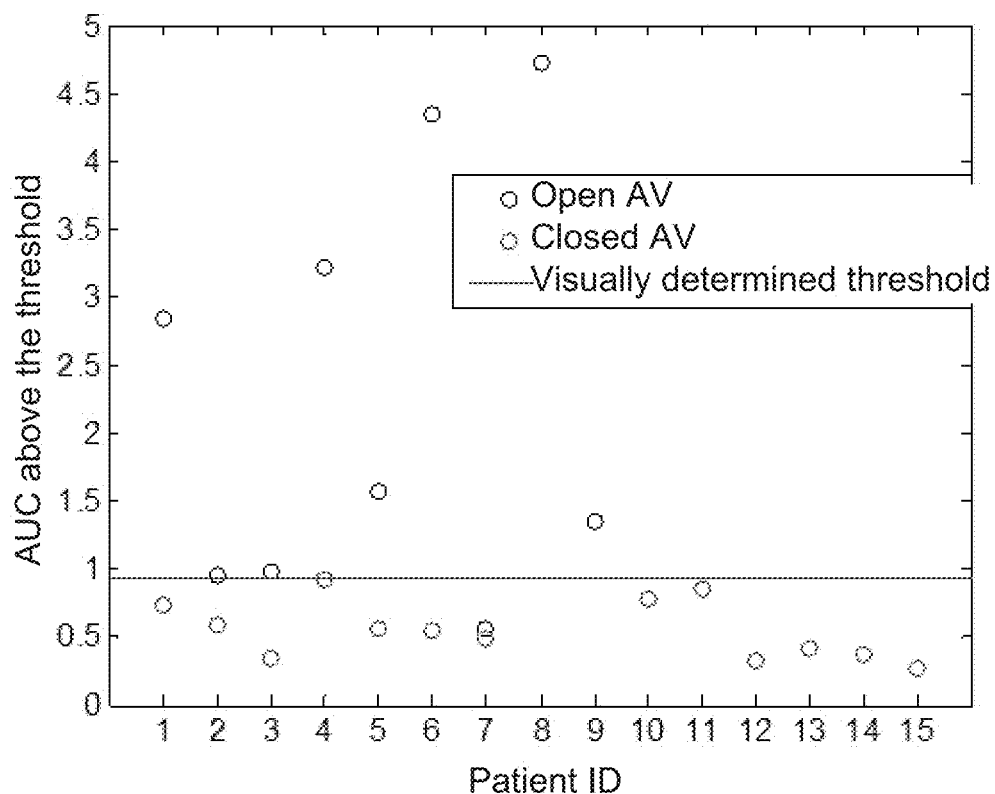
FIG. 9 is a graph of example area under curve (AUC) values above a threshold determined for a number of subjects; and, FIGS. 10A to 10M are graphs of a relationship between the duration of aortic valve opening and the AUC for a number of subjects.
Figure 10A:
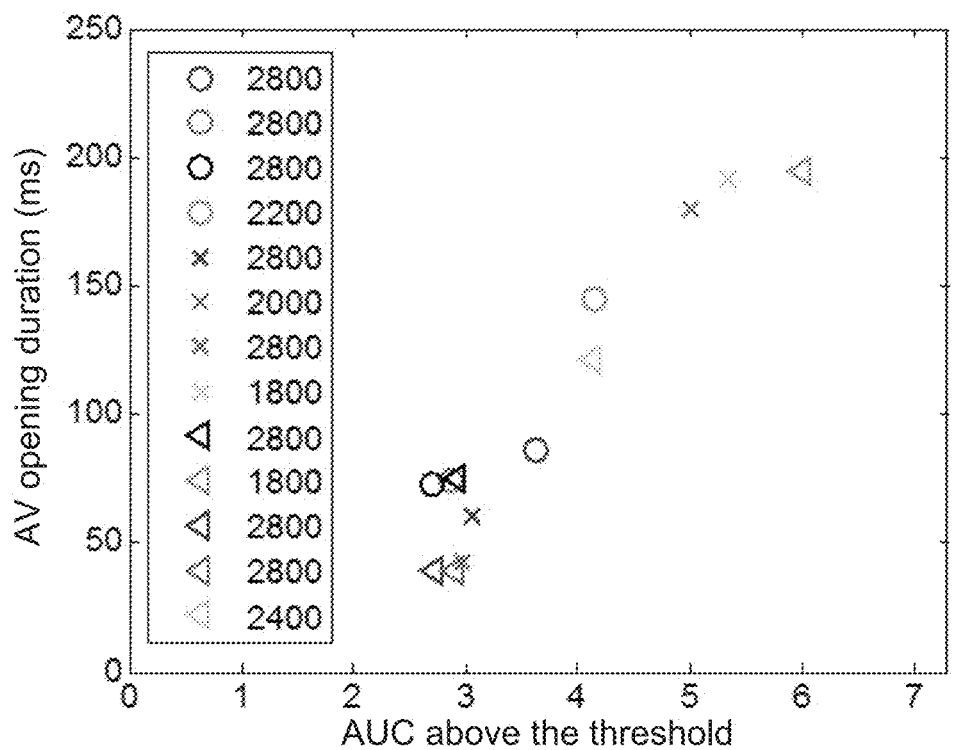
Figure 10B:
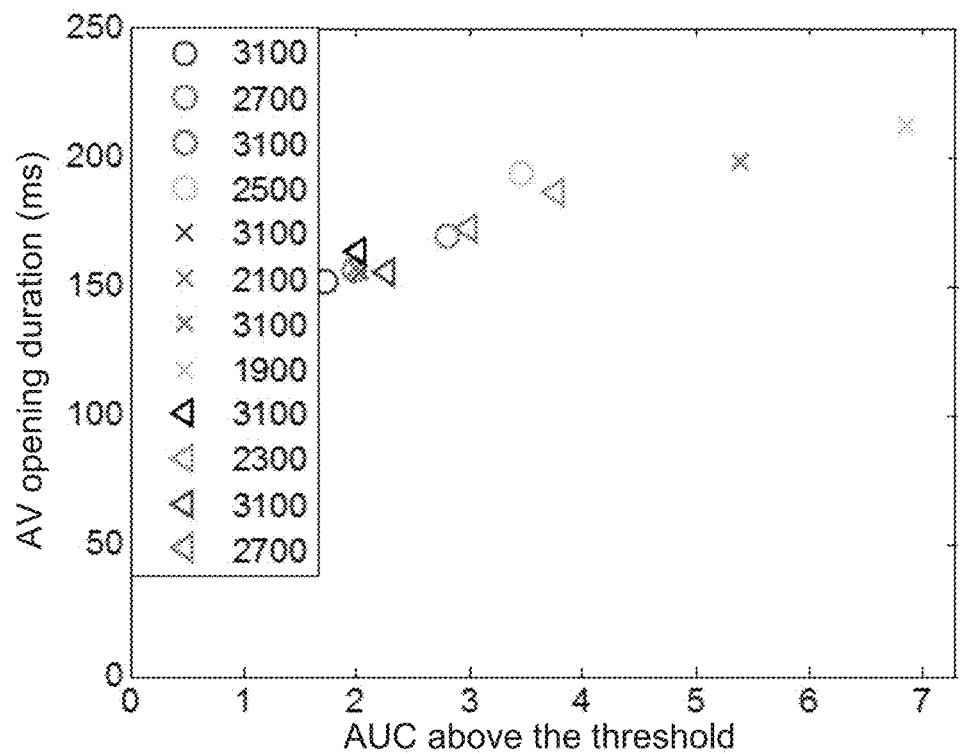
Figure 10C:
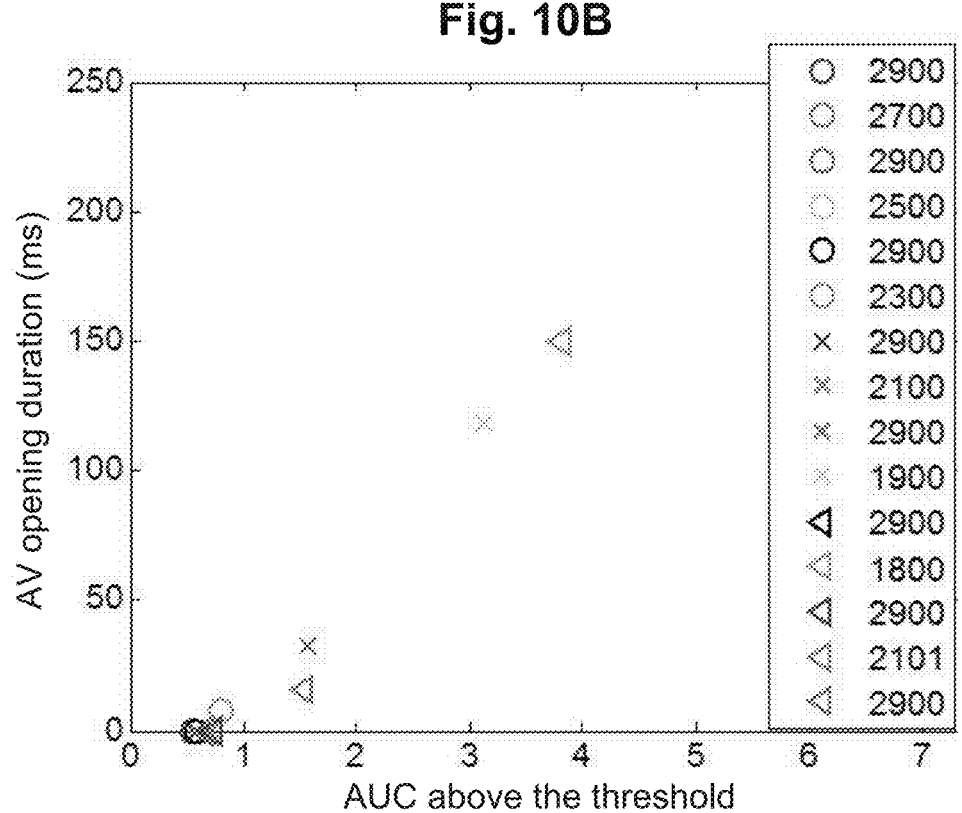
Figure 10D:
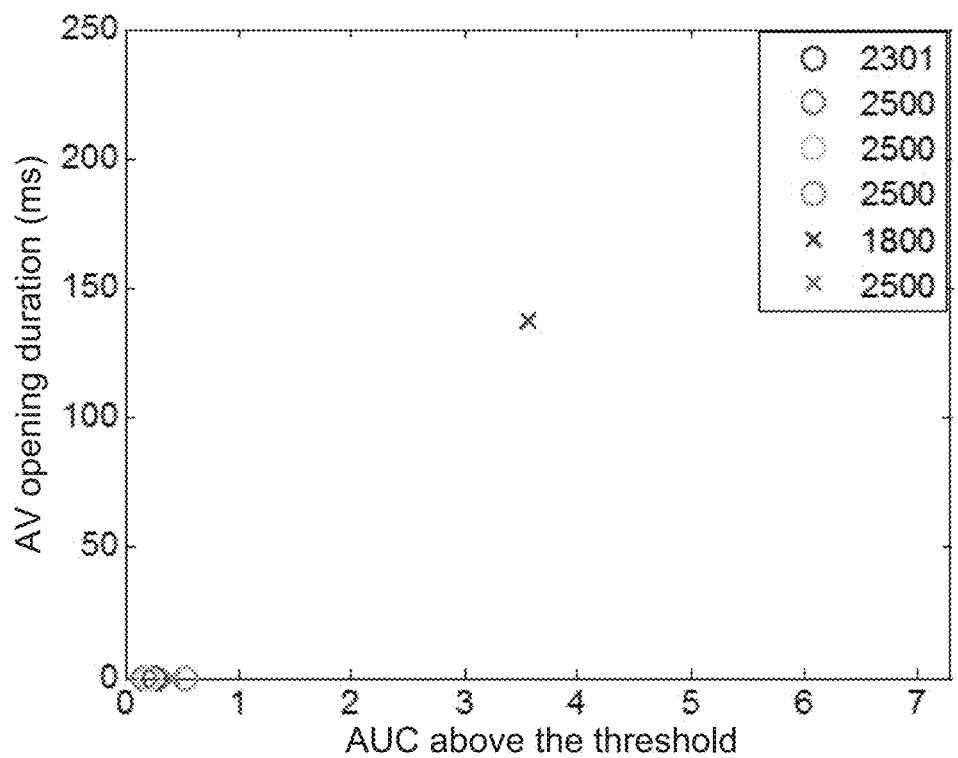
Figure 10E:
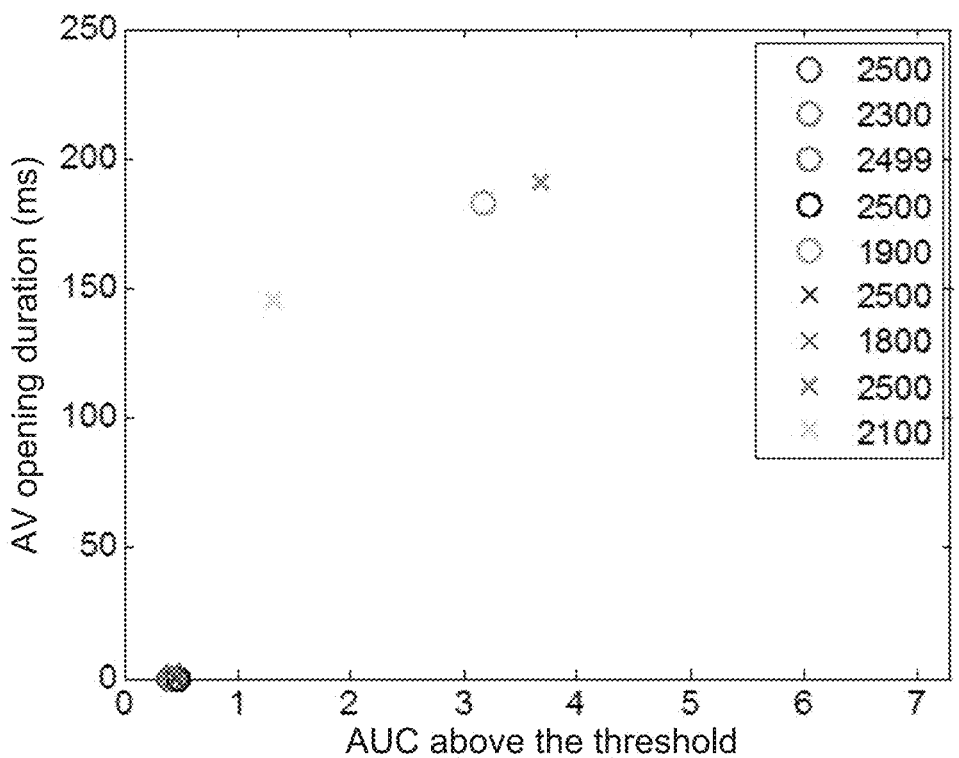
Figure 10F:
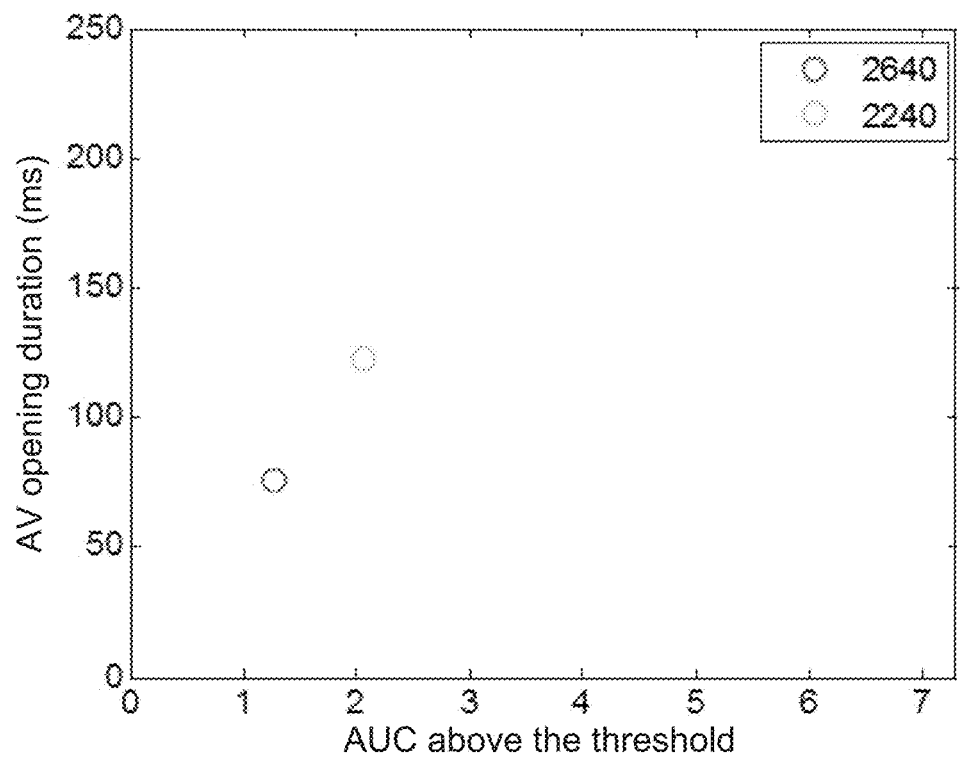
Figure 10G:
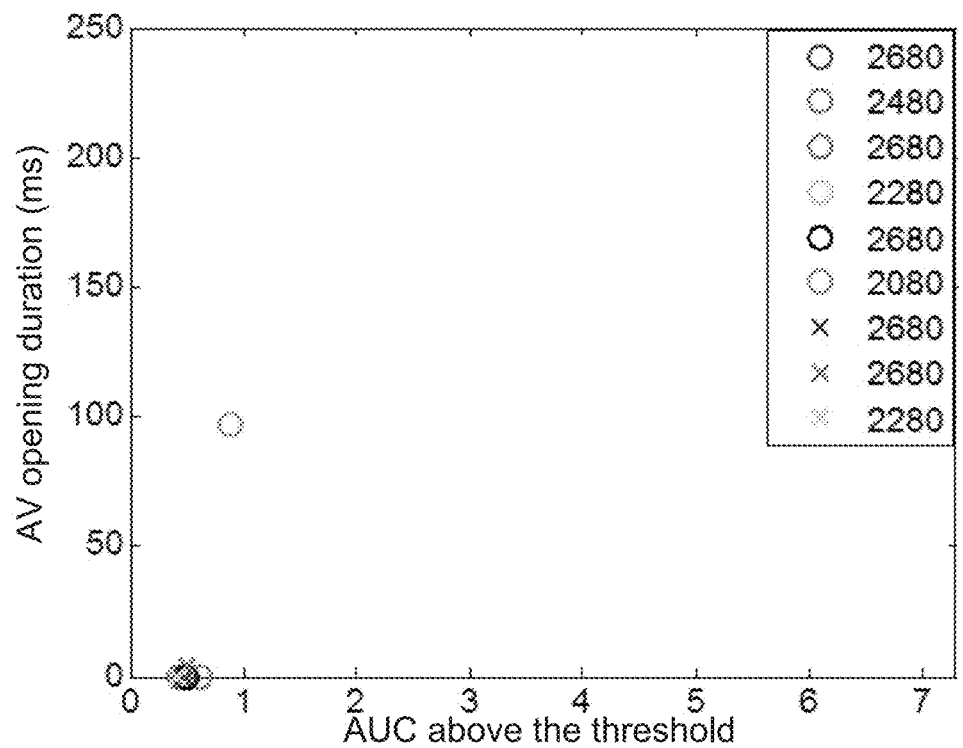
Figure 10H:
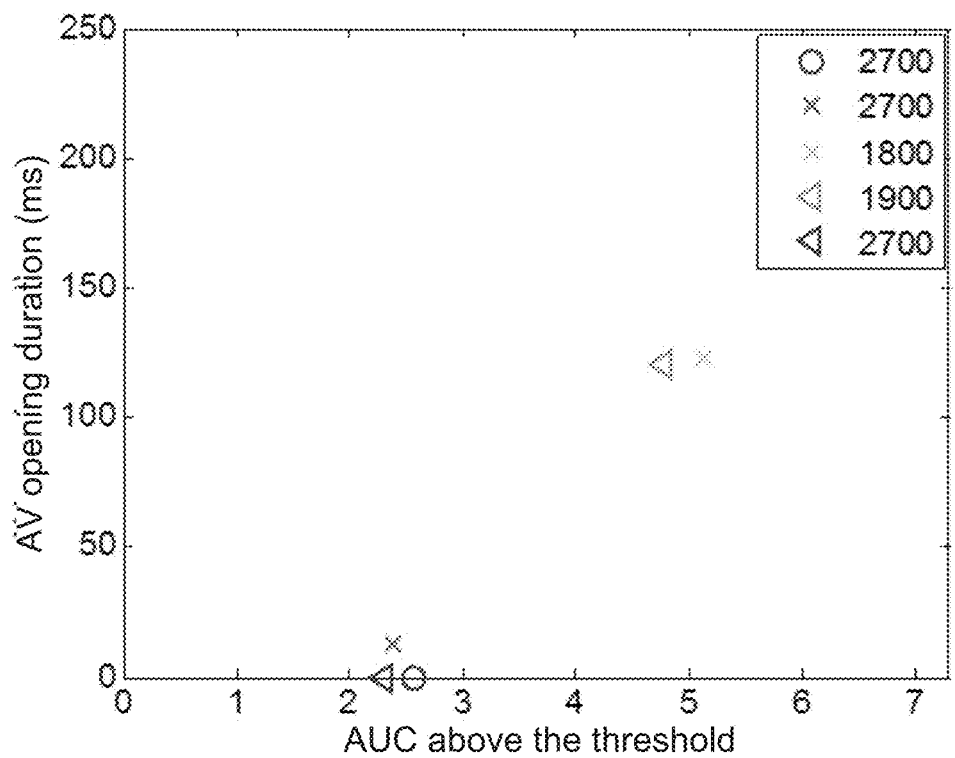
Figure 10I:
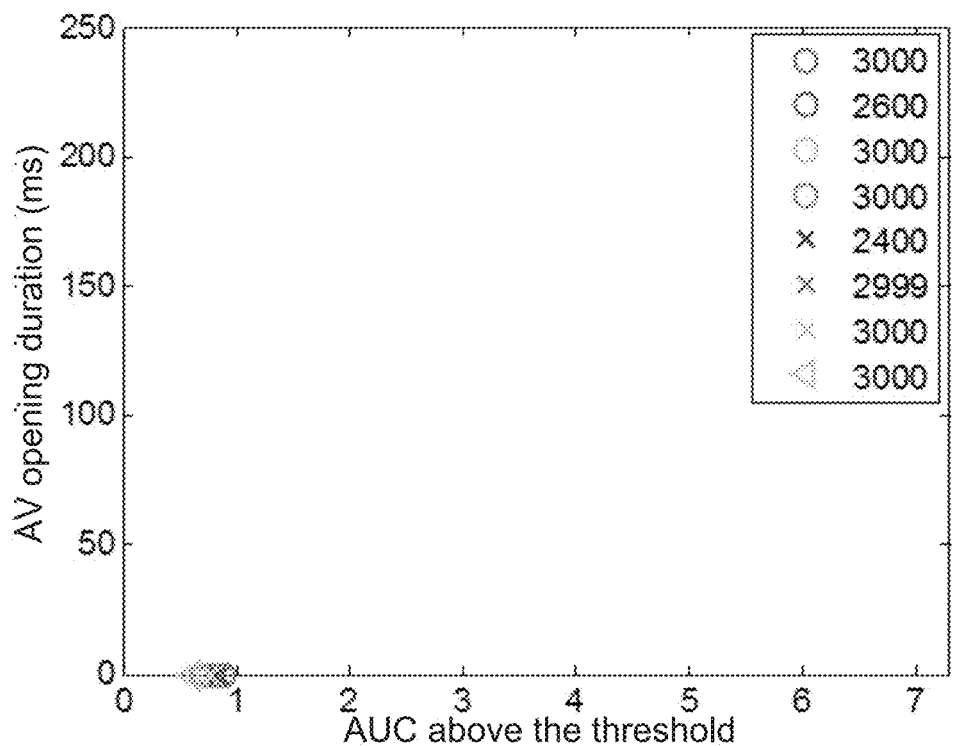
Figure 10J:
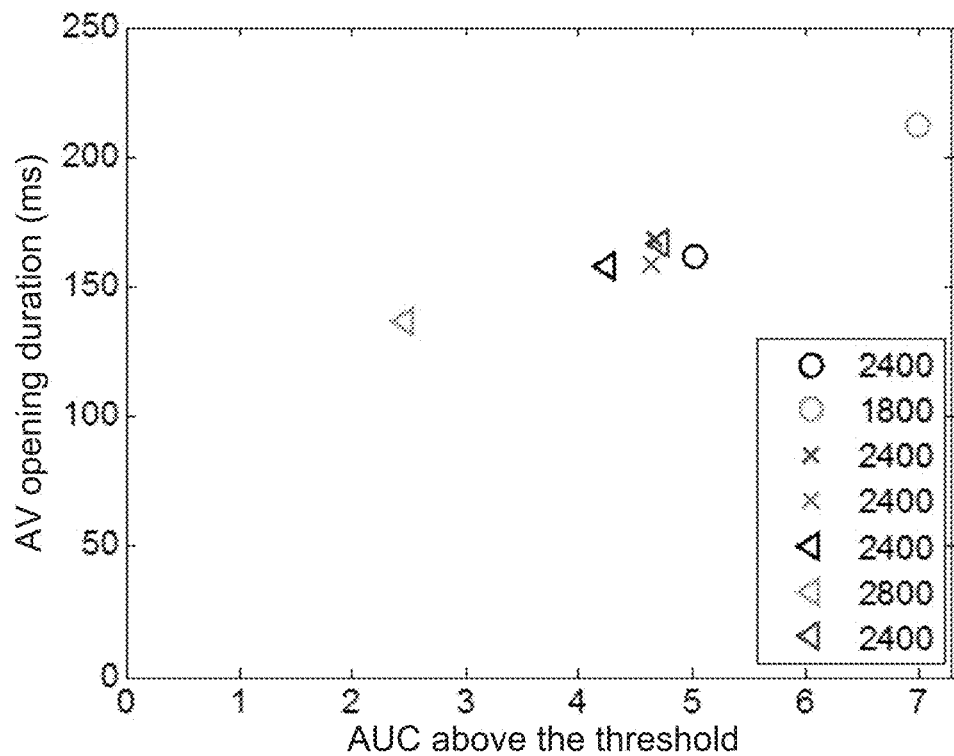
Figure 10K:
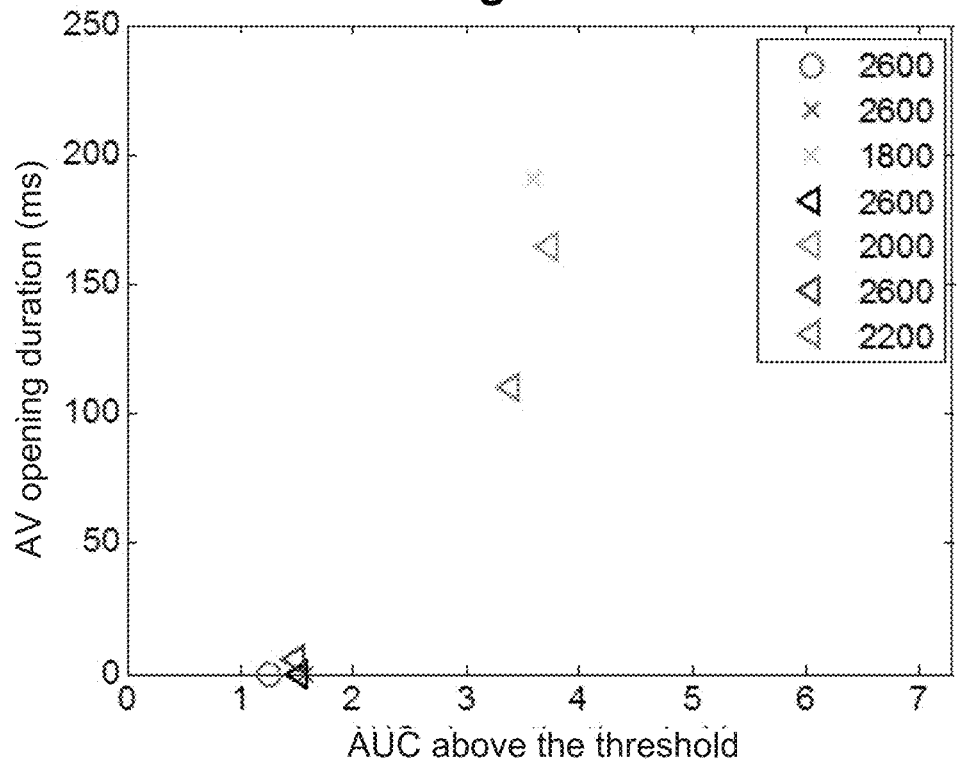
Figure 10L:
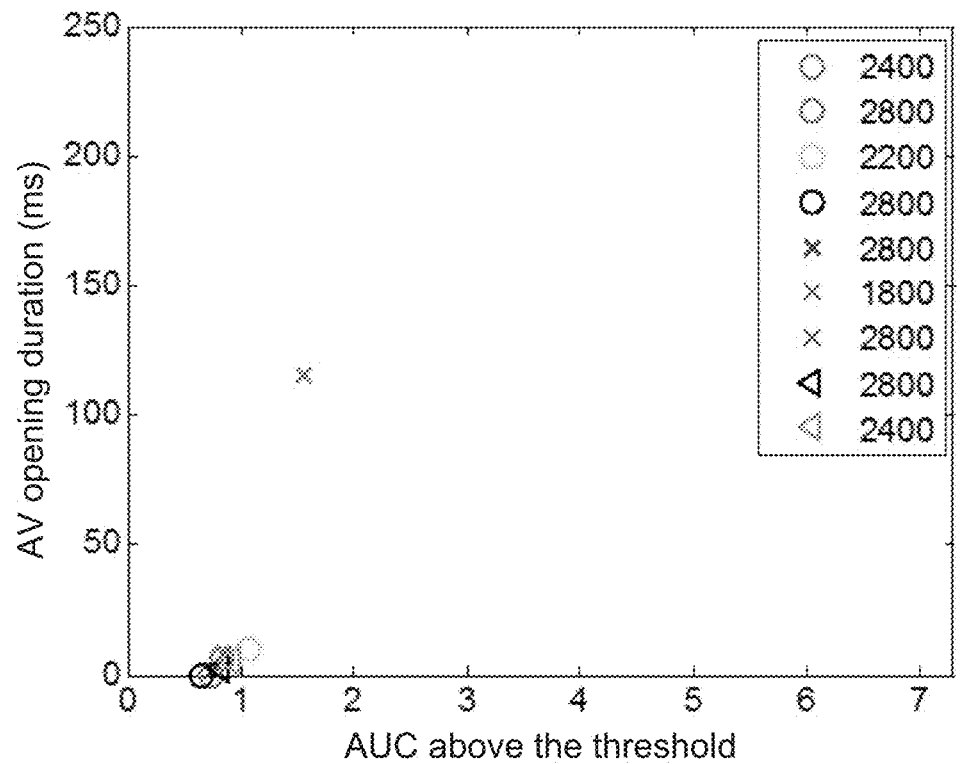
Figure 10M:
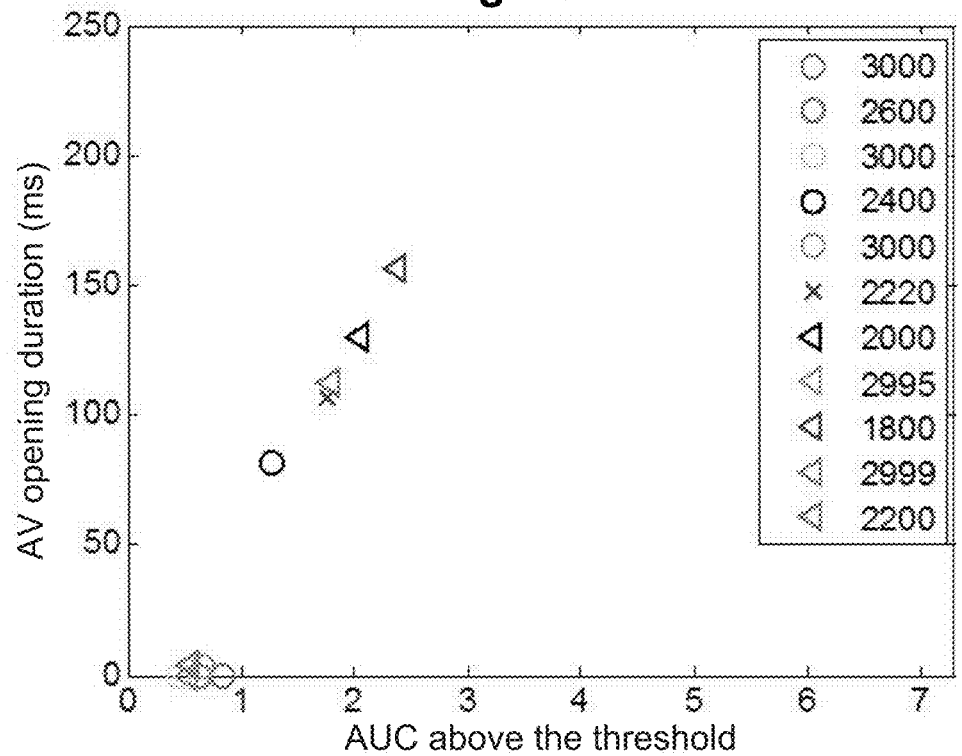

Using the above described methodology, the AUC values above the indicated threshold were determined and are shown in FIG. 9. A visually determined threshold is also indicated between beats with an open and closed aortic valve. It should be noted that in patient 7 the open aortic valve condition was classified as "intermittent", potentially with a slight opening only, and most likely represents a misclassification.

Further analysis of the relationship between the duration of aortic valve opening and the AUC showed a significant relationship in those patients where the status of aortic valve changes from open to closed. For this purpose, pump speed was stepwise reduced from baseline speed by 200, 400, 600, 800, 1000, 1200, 800 and 400 rpm (but not below a minimum speed of 1800 rpm) in 20 second intervals. After each reduction, speed was returned to baseline for a minimal interval of 60 seconds. Using transthoracic echocardiography, the aortic valve state was assessed by performing M-Mode in parasternal long-axis view continuously, placing the sample volume at the level of valve leaflets. A video was continuously acquired via the output of the ultrasound device for subsequent beat-to-beat offline analysis. During this analysis the opening time of the aortic valve in beats with sufficient ultrasound quality was assessed.

FIGS. 10A to 10M indicate the relationship between the aortic valve opening time and the AUC values in thirteen of the fifteen patients. It can be observed that in all of the patients a rather linear relationship between the opening time and the AUC is present, indicating that it is possible to determine a linear relationship between the AUC and the time of valve opening. It should also be noted however that the parameters of the relationship vary in each patient, meaning that it may be necessary to derive patient specific relationships in the event that a degree of valve opening is to be accurately quantified.

In any event, it will be appreciated that the above described methodology allows aortic valve opening to be quantified solely through detection of pump speed changes, thereby obviating the need for additional sensors. This in turn allows additional information regarding cardiac function to be more easily and accurately determined.

Throughout this specification and claims which follow, unless the context requires otherwise, the word "comprise", and variations such as "comprises" or "comprising", will be understood to imply the inclusion of a stated integer or group of integers or steps but not the exclusion of any other integer or group of integers.

Persons skilled in the art will appreciate that numerous variations and modifications will become apparent. All such variations and modifications which become apparent to persons skilled in the art, should be considered to fall within the spirit and scope that the invention broadly appearing before described.

The claims defining the invention are as follows:

1. Apparatus for determining opening of an aortic valve of a biological subject, the apparatus including an electronic processing device that:
   a) determines a pump speed of a ventricular assist device that is assisting cardiac function of the biological subject;
   b) analyses the pump speed to determine a pump speed indicator at least partially indicative of changes in pump speed; and, c) uses the pump speed indicator to determine an opening indicator indicative of opening of the aortic valve.

2. Apparatus according to claim 1, wherein the electronic processing device:
   a) compares the pump speed indicator to at least one threshold; and,
   b) determines the opening indicator in response to the results of the comparison.

3. Apparatus according to claim 2, wherein the pump speed indicator is at least one of:
   a) a distribution, and wherein the electronic processing device determines the threshold based on a maximum value of the distribution;
   b) a power spectral density distribution and wherein the electronic processing device:
      i) determines a maximum power frequency corresponding to the frequency having a maximum power in the power spectral density distribution; and,
      ii) determines the threshold based on the maximum power frequency;
   c) a distribution of rates of change of pump speed and wherein the electronic processing device:
      i) determines a portion of the distribution greater than the threshold; and,
      ii) determines the opening indicator using the portion.

4. Apparatus according to claim 3, wherein the electronic processing device:
   a) calculates an area under curve for the portion; and,
   b) uses the area under curve to determine the opening indicator.

5. Apparatus according to claim 1, wherein the electronic processing device:
   a) determines a pump speed of the ventricular assist device for a plurality of cardiac cycles; and,
   b) at least one of:
      i) determines an opening indicator for at least one of the plurality of cardiac cycles; and,
      ii) determines an opening indicator for at least one of the plurality of cardiac cycles by:
         1) determining the flow rate of blood through the ventricular assist device; and,
         2) using the rate of flow of blood to identify individual cardiac cycles.

6. Apparatus according to claim 5, wherein the electronic processing device identifies individual cardiac cycles from flow rate minima.

7. Apparatus according to claim 1, wherein the electronic processing device at least one of:
   a) records the opening indicator; and,
   b) displays a representation of the opening indicator; and,
   c) uses the opening indicator to at least partially determine a hemodynamic parameter value indicative of at least one of:
      i) an intra-cardiac pressure;
      ii) an atrial pressure;
      iii) a ventricular filling pressure;
      iv) a pulmonary capillary wedge pressure;
      v) a ventricular end diastole pressure;
      vi) a mean arterial pressure;
      vii) ventricular contractility properties; and,
      viii) ventricular relaxation properties.

8. Apparatus according to claim 1, wherein the electronic processing device determines the pump speed at least one of:
   a) in accordance with signals received from a sensor; and,
   b) by receiving pump speed data from a ventricular assist device controller.

9. Apparatus according to claim 1, wherein the electronic processing device:
   a) determines pump speed data indicative of the speed of the ventricular assist device pump; and,
   b) at least one of:
      i) performs a frequency transform on the speed data to determine the speed indicator; and,
      ii) performs a frequency transform on the speed data to determine the speed indicator by:
         1) filtering the pump speed data to remove high frequency components; and,
         2) determining the pump speed indicator using the filtered pump speed data.

10. Apparatus according to claim 9, wherein the electronic processing device:
    a) applies a window function to the pump speed data to create a window of pump speed data; and,
    b) generates a power spectral density distribution using the window of pump speed data.

11. Apparatus according to claim 1, wherein the electronic processing device is at least one of:
    a) controls the ventricular assist device in accordance with the opening indicator;
    b) intermittently controls the pump speed in accordance with the opening indicator; and,
    c) at least one of:
       i) selectively reduces the pump speed to cause opening of the aortic valve; and,
       ii) selectively increases the pump speed to reduce opening of the aortic valve.

12. Apparatus according to claim 11, wherein the electronic processing device:
    a) determines opening indicators over multiple cardiac cycles;
    b) compares a number of cardiac cycles since the aortic valve last opened to a threshold; and,
    c) selectively controls the pump speed in response to results of the comparison.

13. Apparatus according to claim 11, wherein the electronic processing device progressively reduces the pump speed over successive cardiac cycles until at least one of:
    a) the aortic valve opens; and,
    b) a minimum pump speed is reached.

14. A method for determining opening of an aortic valve of a biological subject, the method including, in an electronic processing device:
    a) determining a pump speed of a ventricular assist device that is assisting cardiac function of the biological subject;
    b) analysing the pump speed to determine a pump speed indicator at least partially indicative of changes in pump speed; and,
    c) using the pump speed indicator to determine an opening indicator indicative of opening of the aortic valve.

15. Apparatus for use with a ventricular assist device that is assisting cardiac function of a biological subject, the apparatus including an electronic processing device that:
    a) determines a pump speed of the ventricular assist device over at least one cardiac cycle;
    b) analyses the pump speed to determine a pump speed indicator at least partially indicative of changes in pump speed; and,
    c) uses the pump speed indicator to at least one of:
       i) determine an opening indicator indicative of opening of the aortic valve; and,
       ii) control the ventricular assist device.

16. A method for use with a ventricular assist device that is assisting cardiac function of a biological subject, the method including:
  a) determining a pump speed of the ventricular assist device over at least one cardiac cycle;
  b) analysing the pump speed to determine a pump speed indicator at least partially indicative of changes in pump speed; and,
  c) using the pump speed indicator to at least one of:
    i) determine an opening indicator indicative of opening of the aortic valve; and,
    ii) control the ventricular assist device.

* * * * *